(12) United States Patent
Denham

(10) Patent No.: US 9,333,069 B2
(45) Date of Patent: May 10, 2016

(54) METHOD AND APPARATUS FOR ATTACHING SOFT TISSUE TO BONE

(75) Inventor: Gregory J. Denham, Warsaw, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 675 days.

(21) Appl. No.: 13/273,939

(22) Filed: Oct. 14, 2011

(65) Prior Publication Data

US 2013/0096678 A1     Apr. 18, 2013

(51) Int. Cl.
| | |
|---|---|
| A61F 2/08 | (2006.01) |
| A61B 17/56 | (2006.01) |
| A61B 17/04 | (2006.01) |
| A61B 17/064 | (2006.01) |
| A61B 17/86 | (2006.01) |
| A61B 17/06 | (2006.01) |

(52) U.S. Cl.
CPC ........... *A61F 2/0811* (2013.01); *A61B 17/0401* (2013.01); *A61B 17/0642* (2013.01); *A61B 17/0643* (2013.01); *A61B 17/86* (2013.01); *A61B 2017/0406* (2013.01); *A61B 2017/0414* (2013.01); *A61B 2017/0417* (2013.01); *A61B 2017/0419* (2013.01); *A61B 2017/0427* (2013.01); *A61B 2017/0641* (2013.01); *A61B 2017/06185* (2013.01); *A61F 2002/0829* (2013.01); *A61F 2002/0858* (2013.01); *A61F 2002/0882* (2013.01)

(58) Field of Classification Search
CPC .............. A61F 2/0811; A61F 2/30749; A61B 17/0401; A61B 17/80; A61B 17/8004; A61B 17/82; A61B 17/0487; A61B 17/0643; A61B 17/122; A61B 17/58; A61B 17/56

USPC ....... 623/13.14; 606/71, 79, 84, 86 R, 88, 96, 606/151, 232
See application file for complete search history.

(56) References Cited

U.S. PATENT DOCUMENTS

| | | | |
|---|---|---|---|
| 2,248,054 | A | 7/1941 | Decker |
| 2,267,925 | A | 12/1941 | Johnston |

(Continued)

FOREIGN PATENT DOCUMENTS

| | | | |
|---|---|---|---|
| EP | 0042657 | A1 | 12/1981 |
| EP | 0330328 | A1 | 8/1989 |

(Continued)

OTHER PUBLICATIONS

"Bone Mulch Screw Technique" 1996 by Arthrotek, Inc.

(Continued)

*Primary Examiner* — Brian Pellegrino
(74) *Attorney, Agent, or Firm* — Schwegman Lundberg & Woessner, P.A.

(57) ABSTRACT

The present teachings provide for a graft fixation assembly including a base member, a compression member, and a fastener. The base member includes a bone engaging surface and a first graft engaging surface opposite to the bone engaging surface. A plurality of first fixation members extend from the bone engaging surface and are configured to be impacted into bone. The compression member includes a second graft engaging surface and an outer surface opposite to the second graft engaging surface. The fastener is configured to secure the compression member relative to the base member such that a graft between the base member and the compression member is compressed therebetween and secured to the graft fixation assembly.

31 Claims, 22 Drawing Sheets

(56) References Cited

U.S. PATENT DOCUMENTS

| | | |
|---|---|---|
| 2,570,465 A | 10/1951 | Lundholm |
| 3,208,450 A | 9/1965 | Abelson |
| 3,832,931 A | 9/1974 | Talan |
| 3,896,500 A * | 7/1975 | Rambert et al. ........... 623/13.14 |
| 3,976,079 A * | 8/1976 | Samuels et al. ............... 606/232 |
| 4,278,091 A | 7/1981 | Borzone |
| 4,341,206 A | 7/1982 | Perrett et al. |
| 4,522,202 A | 6/1985 | Otte et al. |
| 4,592,346 A | 6/1986 | Jurgutis |
| 4,605,414 A | 8/1986 | Czajka |
| 4,744,793 A | 5/1988 | Parr et al. |
| 4,755,183 A | 7/1988 | Kenna |
| 4,793,335 A | 12/1988 | Frey et al. |
| 4,793,355 A | 12/1988 | Crum et al. |
| 4,828,562 A | 5/1989 | Kenna |
| 4,950,270 A | 8/1990 | Bowman et al. |
| 4,960,420 A | 10/1990 | Goble et al. |
| 4,988,351 A | 1/1991 | Paulos et al. |
| 5,013,316 A | 5/1991 | Goble et al. |
| 5,024,669 A | 6/1991 | Peterson et al. |
| 5,047,032 A | 9/1991 | Jellicoe |
| 5,047,034 A | 9/1991 | Sohngen |
| 5,062,843 A | 11/1991 | Mahony, III |
| 5,108,397 A | 4/1992 | White |
| 5,108,431 A | 4/1992 | Mansat et al. |
| 5,112,335 A | 5/1992 | Laboureau et al. |
| 5,152,765 A | 10/1992 | Ross et al. |
| 5,211,647 A | 5/1993 | Schmieding |
| 5,234,434 A | 8/1993 | Goble et al. |
| 5,282,802 A | 2/1994 | Mahony, III |
| 5,306,301 A | 4/1994 | Graf et al. |
| 5,354,300 A | 10/1994 | Goble et al. |
| 5,356,435 A | 10/1994 | Thein et al. |
| 5,376,119 A | 12/1994 | Zimmermann et al. |
| 5,385,567 A | 1/1995 | Goble |
| 5,393,302 A | 2/1995 | Clark et al. |
| RE34,871 E | 3/1995 | McGuire et al. |
| 5,425,767 A | 6/1995 | Steininger et al. |
| 5,431,651 A | 7/1995 | Goble |
| 5,454,811 A | 10/1995 | Huebner |
| 5,456,685 A | 10/1995 | Huebner |
| 5,507,750 A | 4/1996 | Goble et al. |
| D374,286 S | 10/1996 | Goble et al. |
| D374,287 S | 10/1996 | Goble et al. |
| D374,482 S | 10/1996 | Goble et al. |
| D375,791 S | 11/1996 | Goble et al. |
| 5,575,819 A | 11/1996 | Amis |
| 5,628,751 A | 5/1997 | Sander et al. |
| 5,632,748 A | 5/1997 | Beck, Jr. et al. |
| 5,645,588 A | 7/1997 | Graf et al. |
| 5,669,909 A | 9/1997 | Zdeblick et al. |
| 5,674,224 A | 10/1997 | Howell et al. |
| 5,741,266 A | 4/1998 | Moran et al. |
| 5,755,718 A | 5/1998 | Sklar |
| 5,891,150 A | 4/1999 | Chan |
| 5,899,938 A | 5/1999 | Sklar et al. |
| 5,931,869 A | 8/1999 | Boucher et al. |
| 5,941,883 A | 8/1999 | Sklar |
| 5,961,520 A | 10/1999 | Beck, Jr. et al. |
| 6,056,750 A | 5/2000 | Lob et al. |
| 6,077,267 A | 6/2000 | Huene |
| 6,132,433 A | 10/2000 | Whelan |
| 6,132,442 A | 10/2000 | Ferragamo et al. |
| 6,190,390 B1 * | 2/2001 | McAllister ...................... 606/87 |
| 6,231,606 B1 | 5/2001 | Graf et al. |
| 6,254,605 B1 | 7/2001 | Howell |
| 6,280,472 B1 | 8/2001 | Boucher et al. |
| 6,336,940 B1 * | 1/2002 | Graf et al. ................... 623/13.14 |
| 6,364,886 B1 | 4/2002 | Sklar |
| 6,371,988 B1 | 4/2002 | Pafford et al. |
| 6,436,100 B1 | 8/2002 | Berger |
| 6,482,232 B1 | 11/2002 | Boucher et al. |
| 6,498,189 B1 | 12/2002 | Rogelj et al. |
| 6,514,274 B1 * | 2/2003 | Boucher et al. ............... 606/232 |
| 6,533,816 B2 | 3/2003 | Sklar |
| 6,547,778 B1 | 4/2003 | Sklar et al. |
| 6,554,862 B2 | 4/2003 | Hays et al. |
| 6,685,709 B2 | 2/2004 | Sklar |
| 6,699,286 B2 | 3/2004 | Sklar |
| 6,755,840 B2 | 6/2004 | Boucher et al. |
| 6,767,350 B1 | 7/2004 | Lob et al. |
| 7,090,676 B2 * | 8/2006 | Huebner et al. .................. 606/71 |
| 7,112,221 B2 * | 9/2006 | Harris ............................ 606/151 |
| 7,211,111 B2 | 5/2007 | Boucher et al. |
| 7,500,983 B1 * | 3/2009 | Kaiser et al. ................. 606/232 |
| 7,510,566 B2 * | 3/2009 | Jacobs et al. .................. 606/215 |
| 7,658,741 B2 | 2/2010 | Claypool et al. |
| 7,722,644 B2 * | 5/2010 | Fallin et al. .................... 606/232 |
| 7,927,343 B2 * | 4/2011 | Hill et al. ....................... 606/151 |
| 8,221,498 B2 | 7/2012 | Boucher et al. |
| 2001/0047206 A1 | 11/2001 | Sklar et al. |
| 2002/0042615 A1 | 4/2002 | Graf et al. |
| 2003/0009218 A1 | 1/2003 | Boucher et al. |
| 2003/0130735 A1 * | 7/2003 | Rogalski ..................... 623/13.14 |
| 2009/0265014 A1 | 10/2009 | May et al. |
| 2011/0098727 A1 | 4/2011 | Kaiser et al. |
| 2012/0016474 A1 | 1/2012 | Boucher et al. |
| 2012/0283832 A1 | 11/2012 | Boucher et al. |

FOREIGN PATENT DOCUMENTS

| | | |
|---|---|---|
| EP | 0358372 A1 | 3/1990 |
| EP | 0408416 A1 | 1/1991 |
| EP | 0409364 A2 | 1/1991 |
| EP | 0630613 A2 | 12/1994 |
| EP | 0893109 A2 | 1/1999 |
| FR | 2702646 A1 | 9/1994 |
| WO | WO-98/22047 A1 | 5/1998 |
| WO | WO-00/04834 A2 | 2/2000 |
| WO | WO 2011150180 A2 * | 12/2011 .......... A61F 2/30749 |

OTHER PUBLICATIONS

"Intrafix" www.jnjgateway.com/home.jhtml?page=viewContent&contentId=fc0de00100001512 printed Apr. 14, 2004, by Depuy Mitek a Johnson & Johnson Co. (1 page).

"Trauma Systems," 1990, by Biomet, Inc.

European Search Report mailed Jul. 31, 2008 for European application No. EP 04027643.

Innovasive Devices: "Intrafix Technique fo rTibial Fixation of ACL Grafts," copyright 1999, 6 sheets.

\* cited by examiner

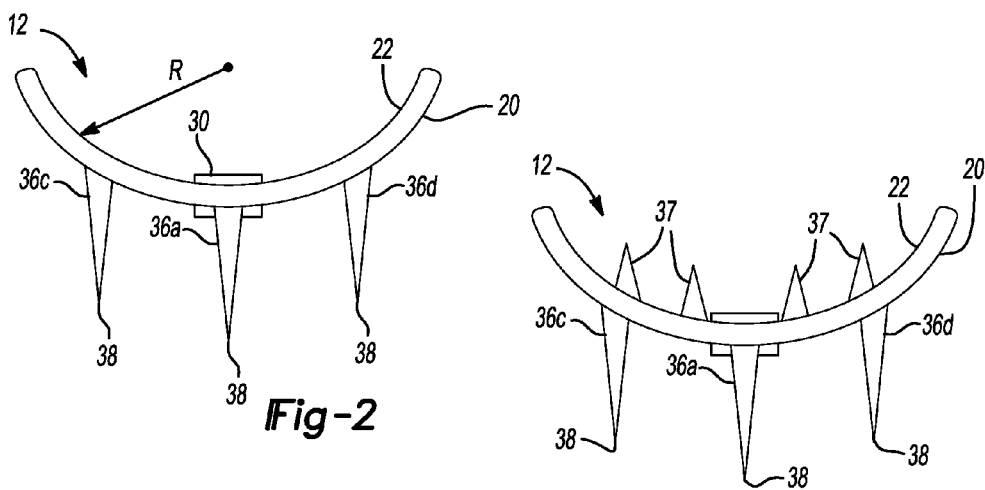
*Fig-2*
*Fig-2A*
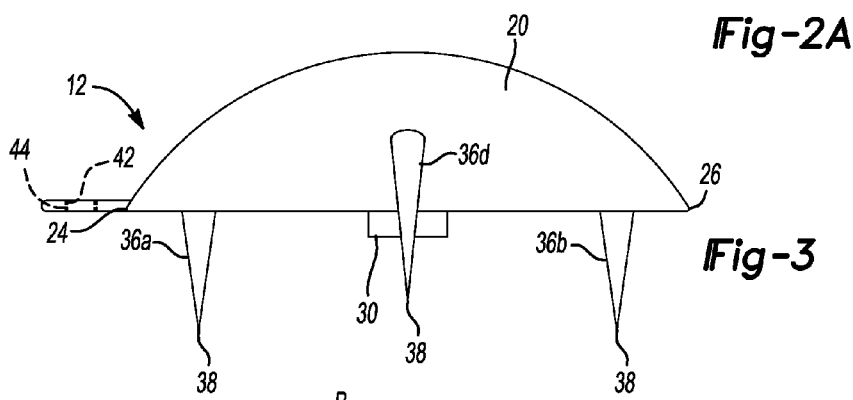
*Fig-3*
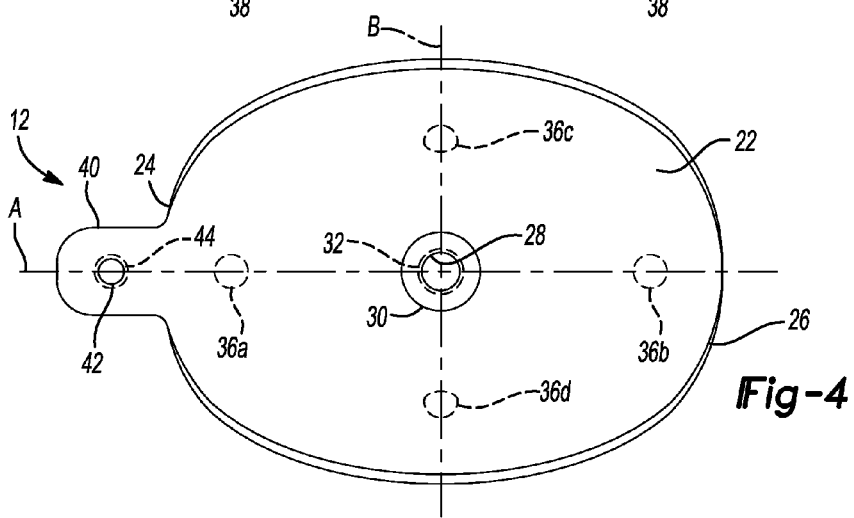
*Fig-4*

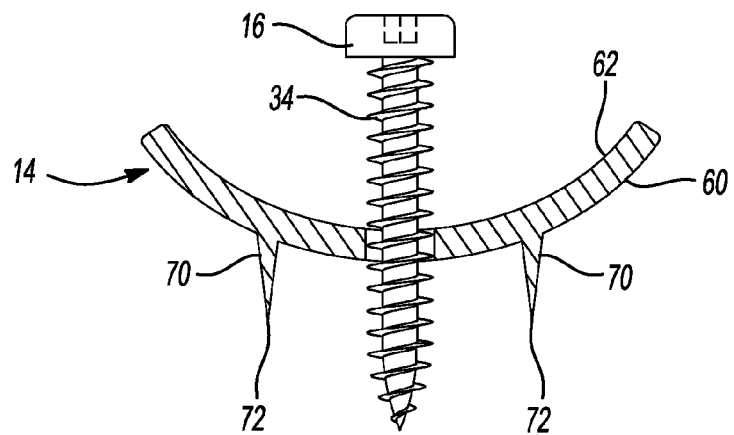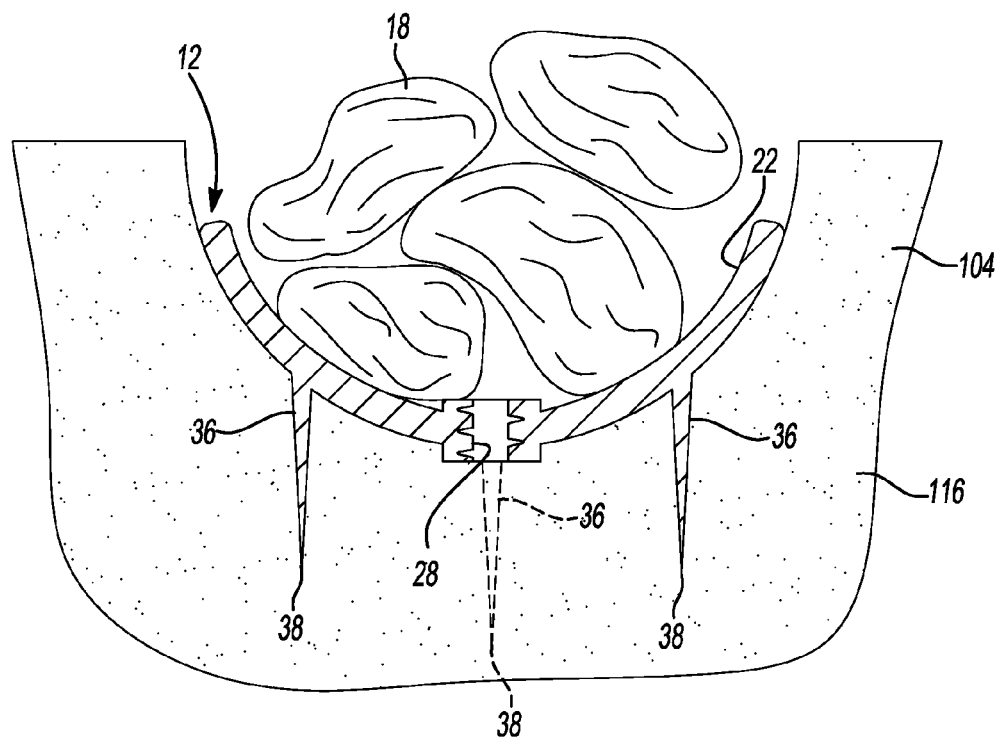
Fig-9

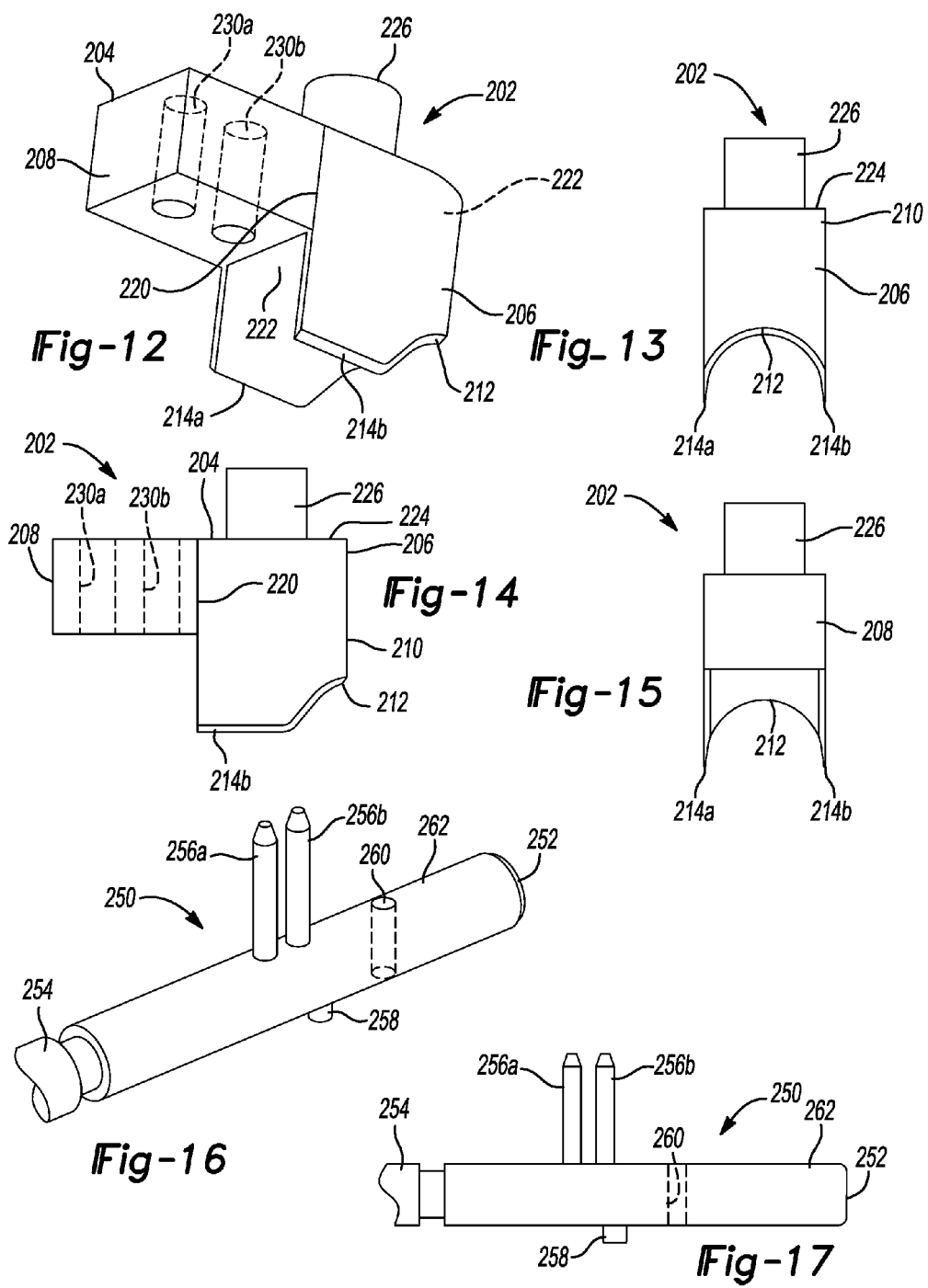

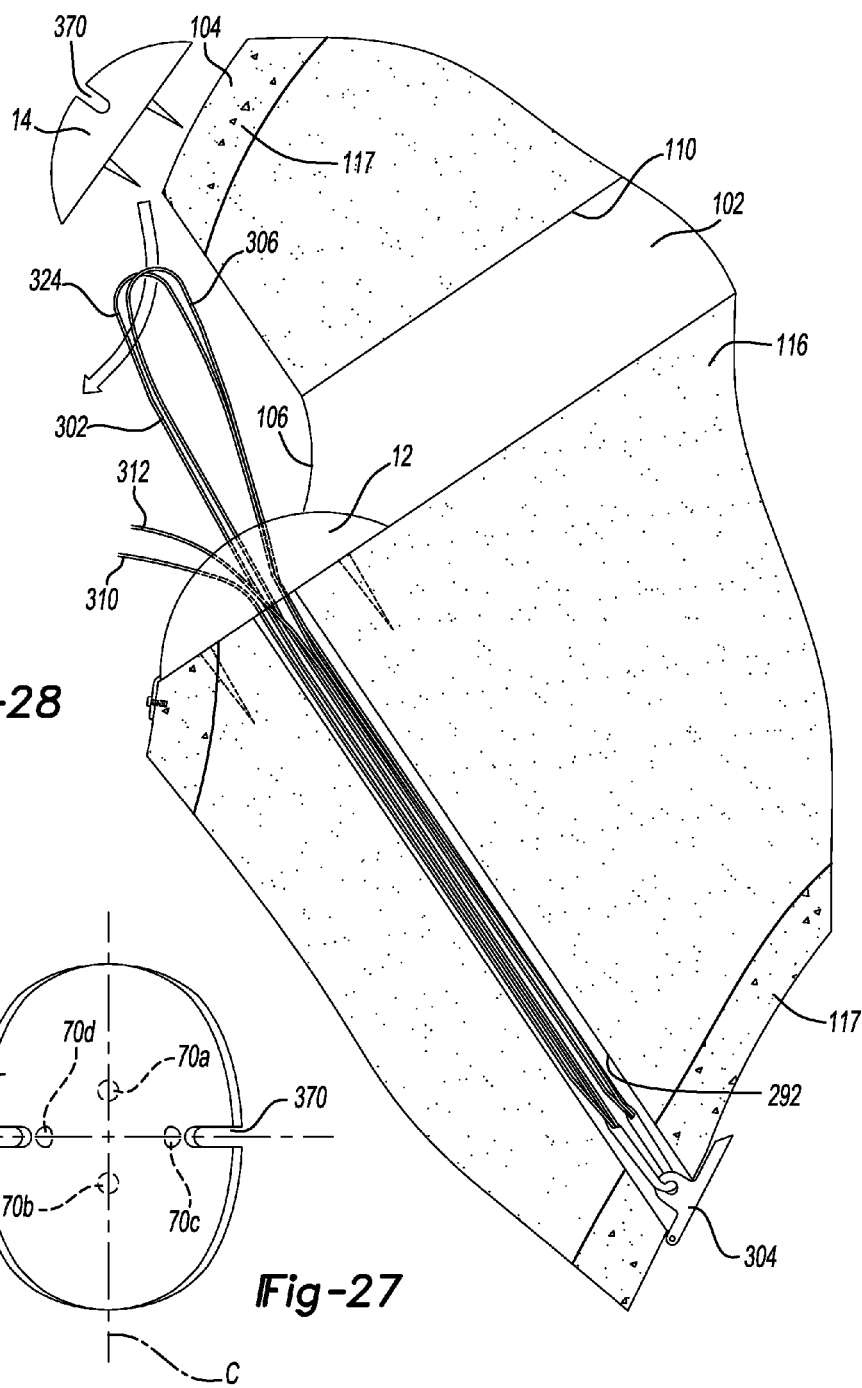

METHOD AND APPARATUS FOR ATTACHING SOFT TISSUE TO BONE

FIELD

The present disclosure relates to methods and apparatus for attaching soft tissue to bone.

BACKGROUND

This section provides background information related to the present disclosure which is not necessarily prior art.

Ligaments are strong fibrous connective soft tissue that connect the articular ends of bones to bind them together and to facilitate or limit motion. Injuries to ligaments are common, and patients who are physically active are generally more susceptible to such ligament injuries. The anterior cruciate ligament (ACL) of the knee joint is a ligament frequently injured by such patients. Such injuries cause instability in the knee joint which, when left untreated, may lead to degenerative arthritis. Because of this condition, ACL reconstruction may be required. Generally during ACL reconstruction, a substitute soft tissue ligament or graft is attached to the femur and/or tibia to facilitate regrowth and permanent attachment.

One way to perform this reconstruction involves the use of a soft tissue ligament graft. Such a graft is generally taken from the hamstring ligament, specifically, the semitendinosus and gracilis ligaments or tendons. Such grafts are generally fed through the ligament tunnel and secured inside or outside the tunnel. Current methods and apparatus for securing the graft in position are suitable for their intended use, but are subject to improvement.

SUMMARY

This section provides a general summary of the disclosure, and is not a comprehensive disclosure of its full scope or all of its features.

The present teachings provide for a graft fixation system including a base member, a compression member, and a fastener. The base member includes a bone engaging surface and a first graft engaging surface opposite to the bone engaging surface. A plurality of first fixation members extend from the bone engaging surface and are configured to be impacted into bone. The compression member includes a second graft engaging surface and an outer surface opposite to the second graft engaging surface. The fastener is configured to secure the compression member relative to the base member such that a graft between the base member and the compression member is compressed therebetween and secured to the graft fixation system.

The present teachings further provide for a method for attaching a soft tissue graft to a tibia bone. The method includes forming a bone tunnel through the tibia bone, the bone tunnel defining an opening at an exterior surface of the tibia bone; impacting a base member of a graft fixation assembly into a posterior wall surface of the bone tunnel proximate to the opening; positioning a graft within the bone tunnel such that the graft extends across the base member; tensioning the graft within the bone tunnel; and compressing the graft between the base member and a compression member by drawing the compression member toward the base member with a fastener.

The present teachings include a further method for attaching a soft tissue graft to a tibia bone. The method includes forming a bone tunnel through the tibia bone, the bone tunnel defining an opening at an exterior surface of the tibia bone; inserting a guide pin into the opening; mounting a cutting device to the guide pin; positioning a cutting blade of the cutting device at an anterior surface of the tibia bone; impacting the cutting blade against the anterior surface of the tibia bone to remove an anterior edge of the tibia bone and increase a size of the opening; impacting a base member of a graft fixation assembly into a posterior surface of the bone tunnel; positioning a graft within the bone tunnel such that the graft extends across the base member; tensioning the graft within the bone tunnel; and compressing the graft between the base member and a compression member of the graft fixation assembly to secure the graft within the bone tunnel.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a front view of a base member of the graft fixation assembly of FIG. 1;

FIG. 2A is a side view of another base member according to the present teachings;

FIG. 3 is a side view of the base member of the graft fixation assembly of FIG. 1;

FIG. 4 is a top view of the base member of the graft fixation assembly of FIG. 1;

FIG. 9 is a cross-sectional view taken along line 9-9 of FIG. 8B;

FIG. 12 is a perspective view of a cutting device of the present teachings;

FIG. 13 is a front view of the cutting device of FIG. 1;

FIG. 14 is a side view of the cutting device of FIG. 1;

FIG. 15 is a rear view of the cutting device of FIG. 1;

FIG. 16 is a perspective view of a guide pin according to the present teachings;

FIG. 17 is a side view of the guide pin of FIG. 16;

FIG. 27 is a top view of a compression member of the present teachings;

FIG. 28 illustrates the graft fixation assembly including the compression member of FIG. 27 being implanted into a tibia bone;

Figure 29:
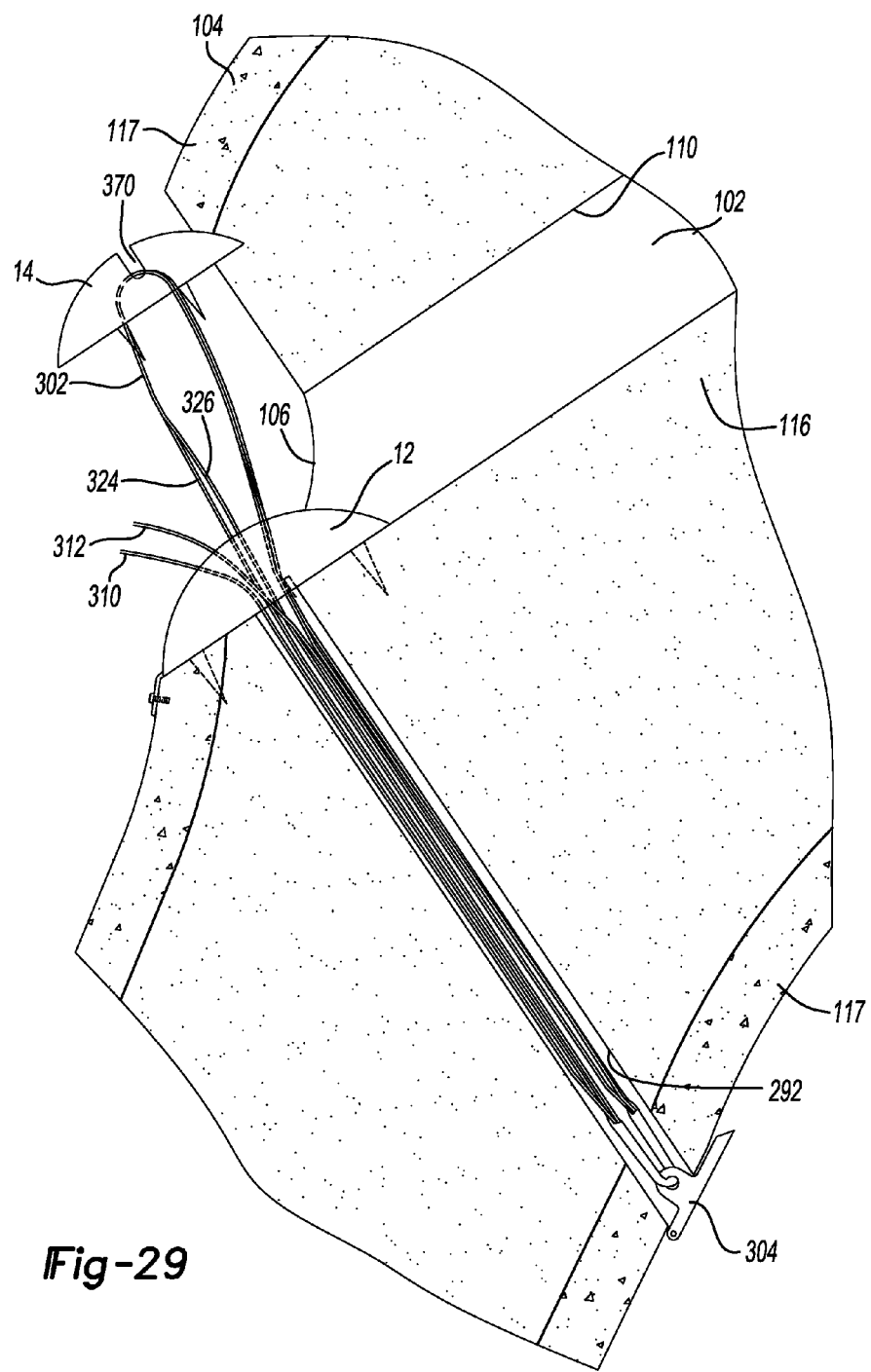
Figure 30:
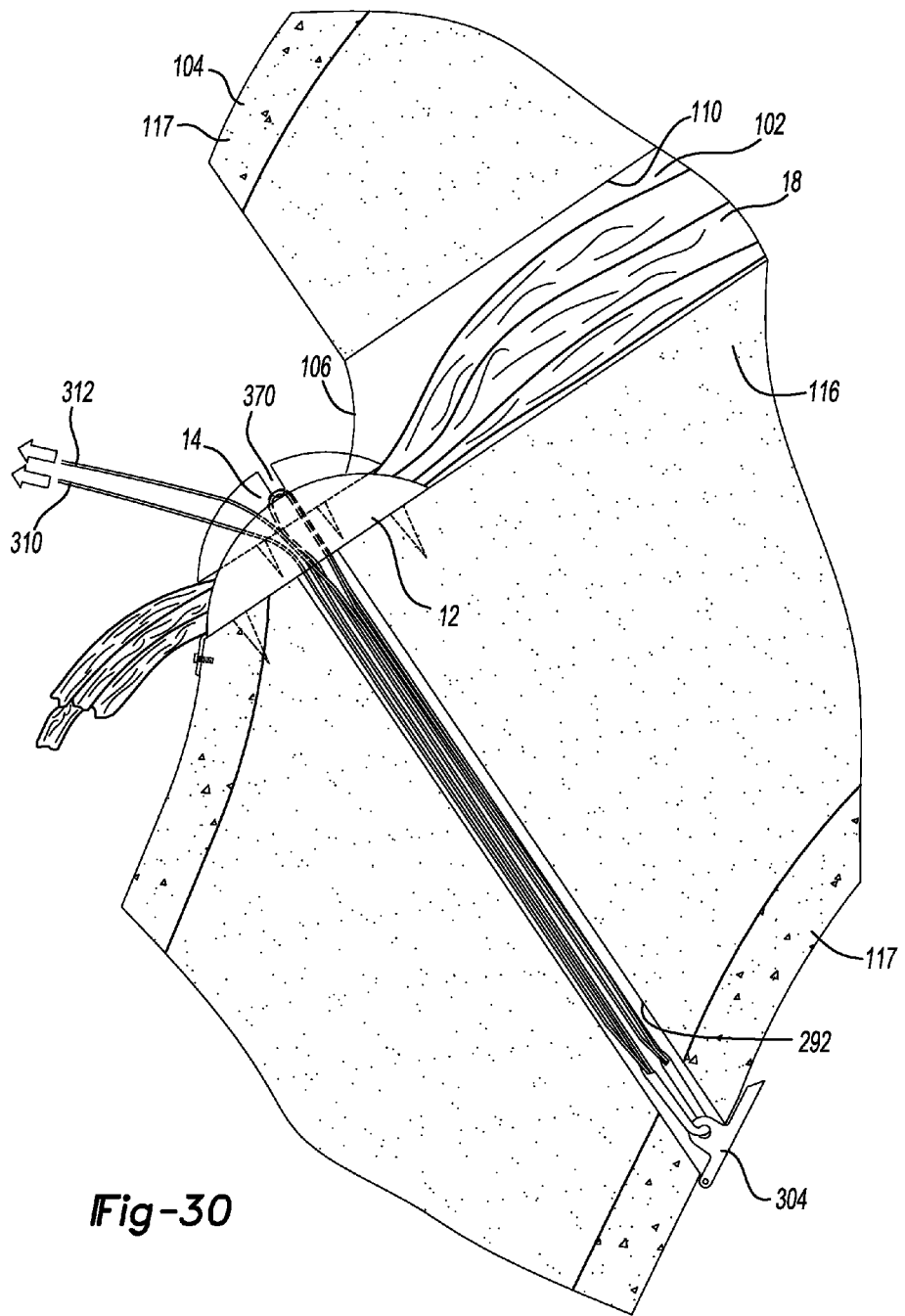
Figure 31:
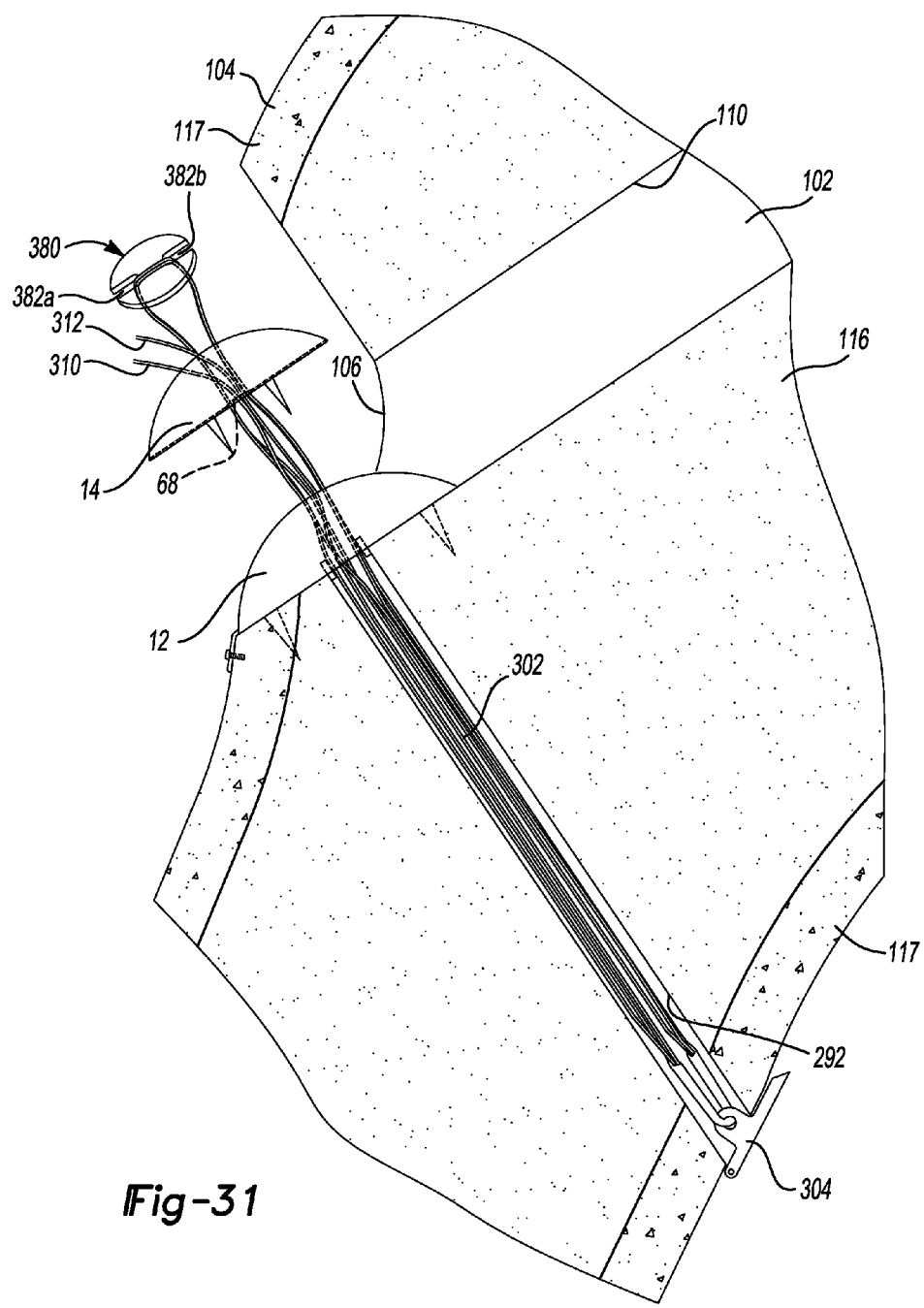
Figure 32:
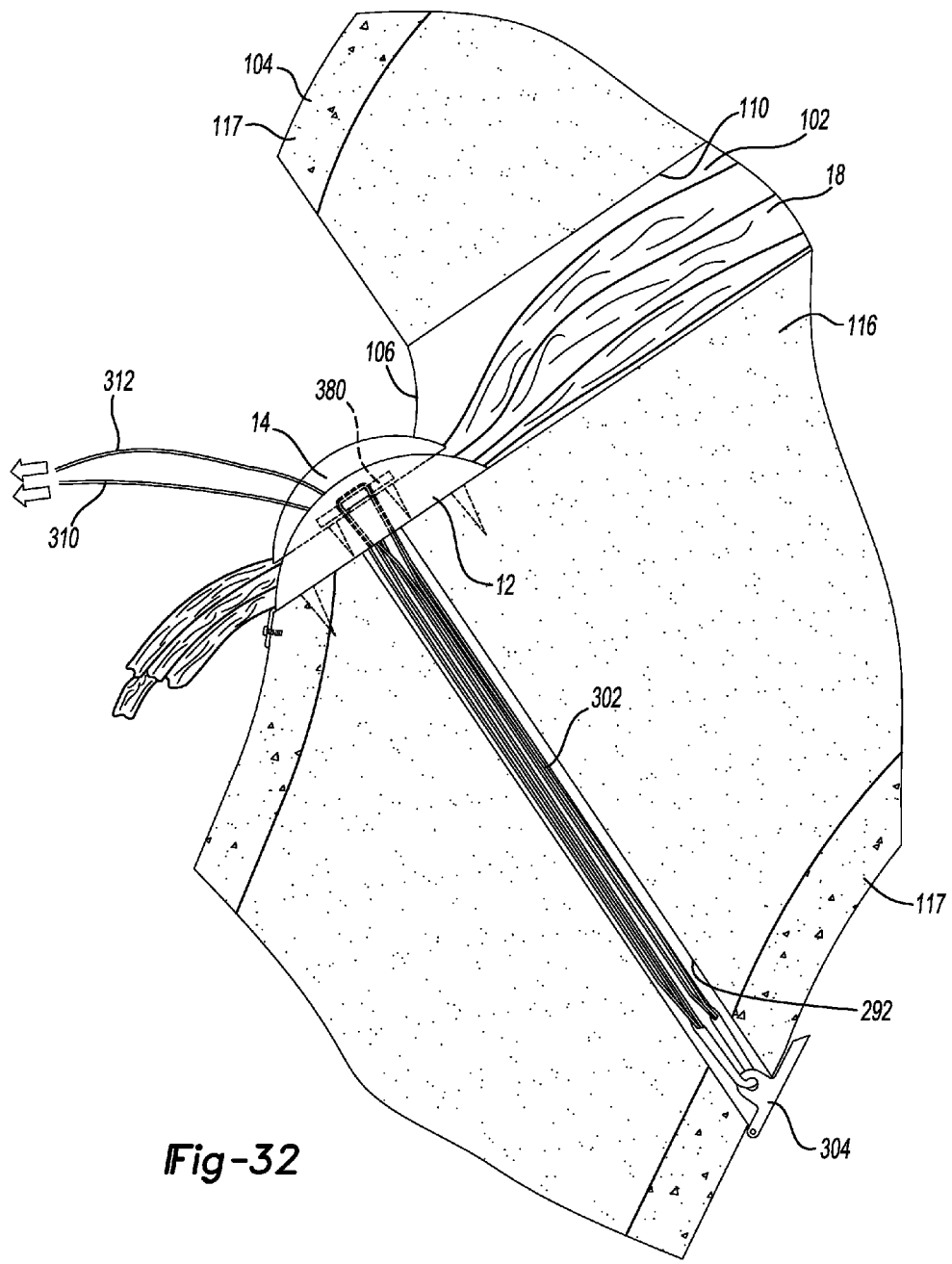
Figure 33:
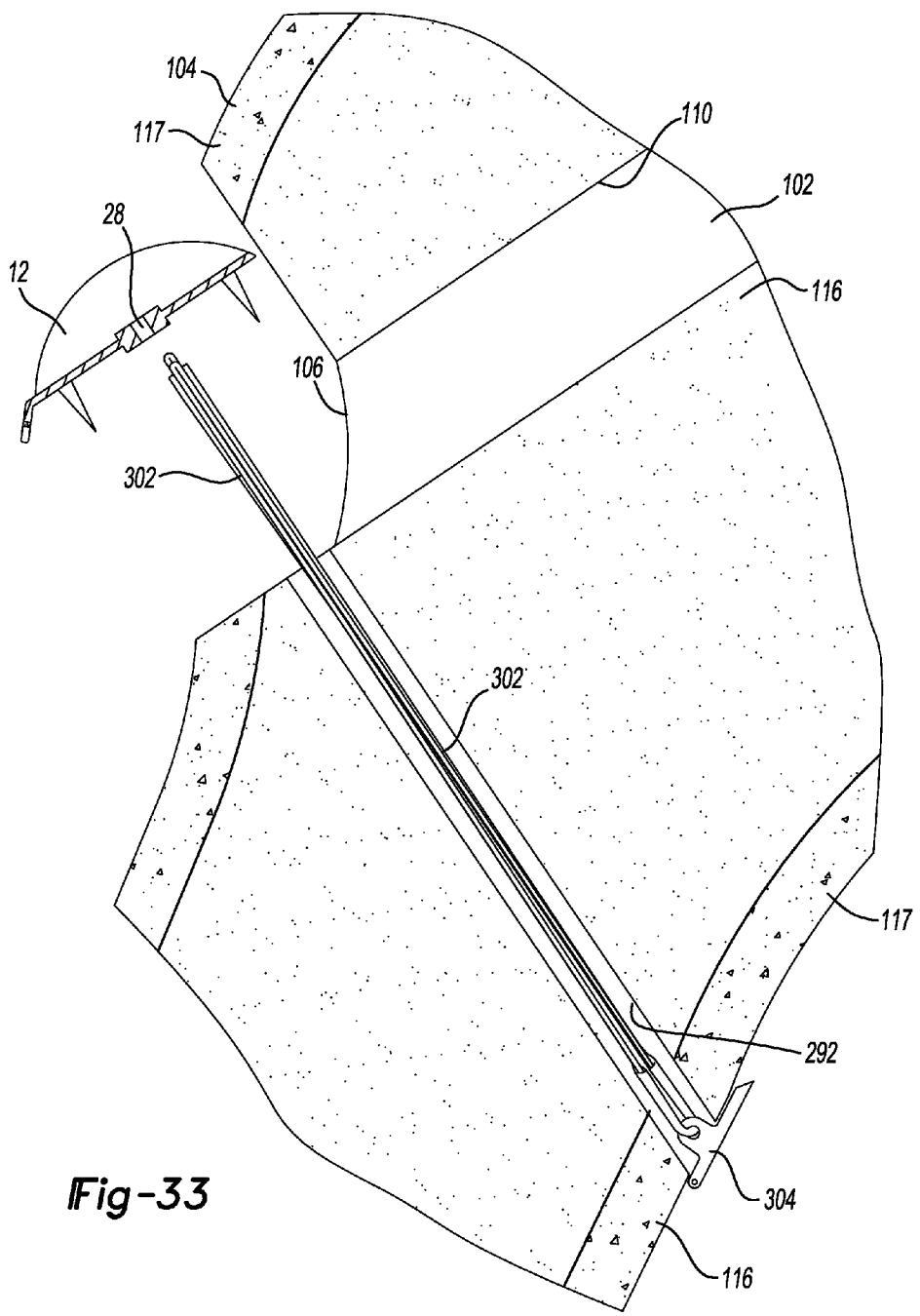
Figure 34:
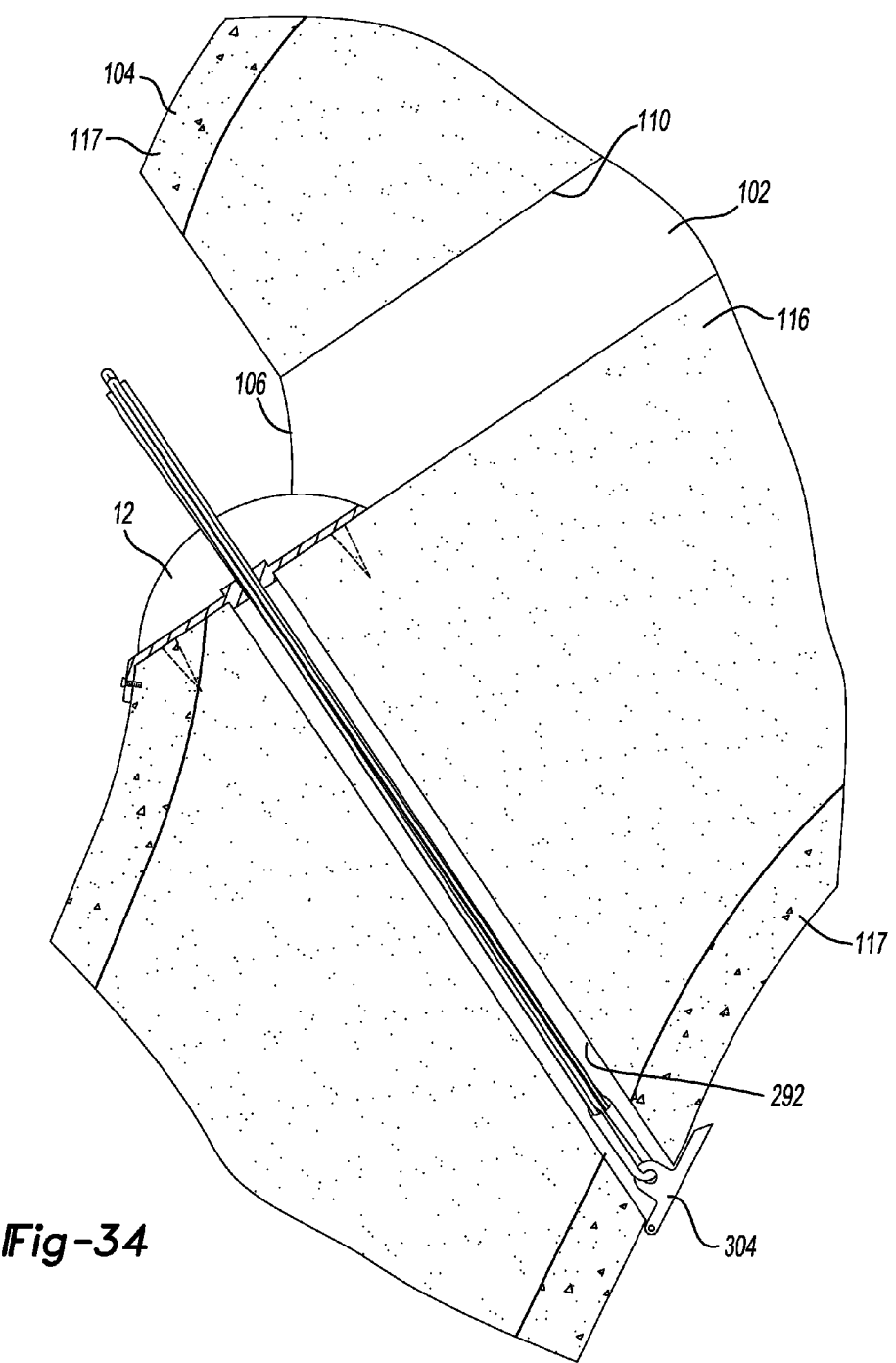
Figure 35:
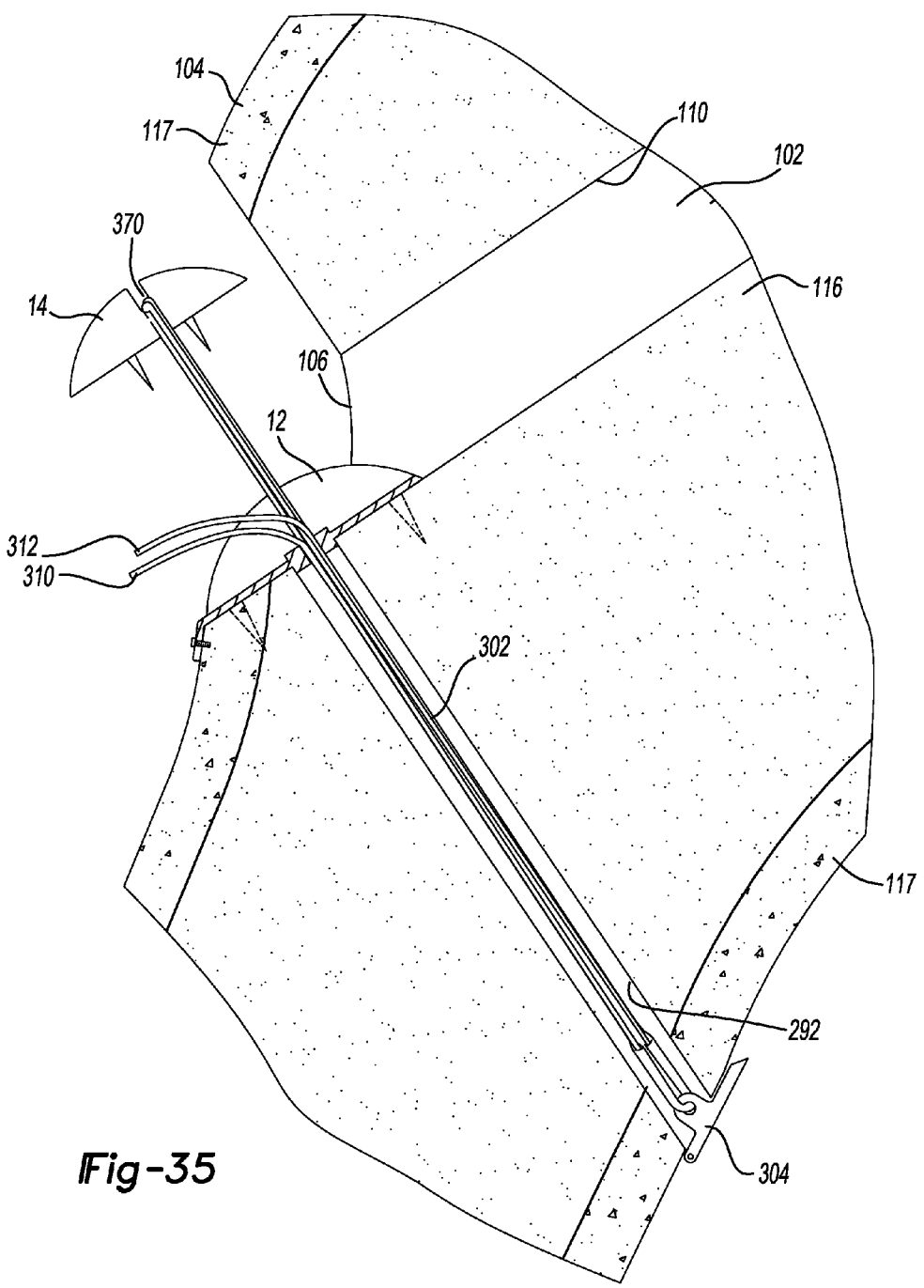
Figure 36:
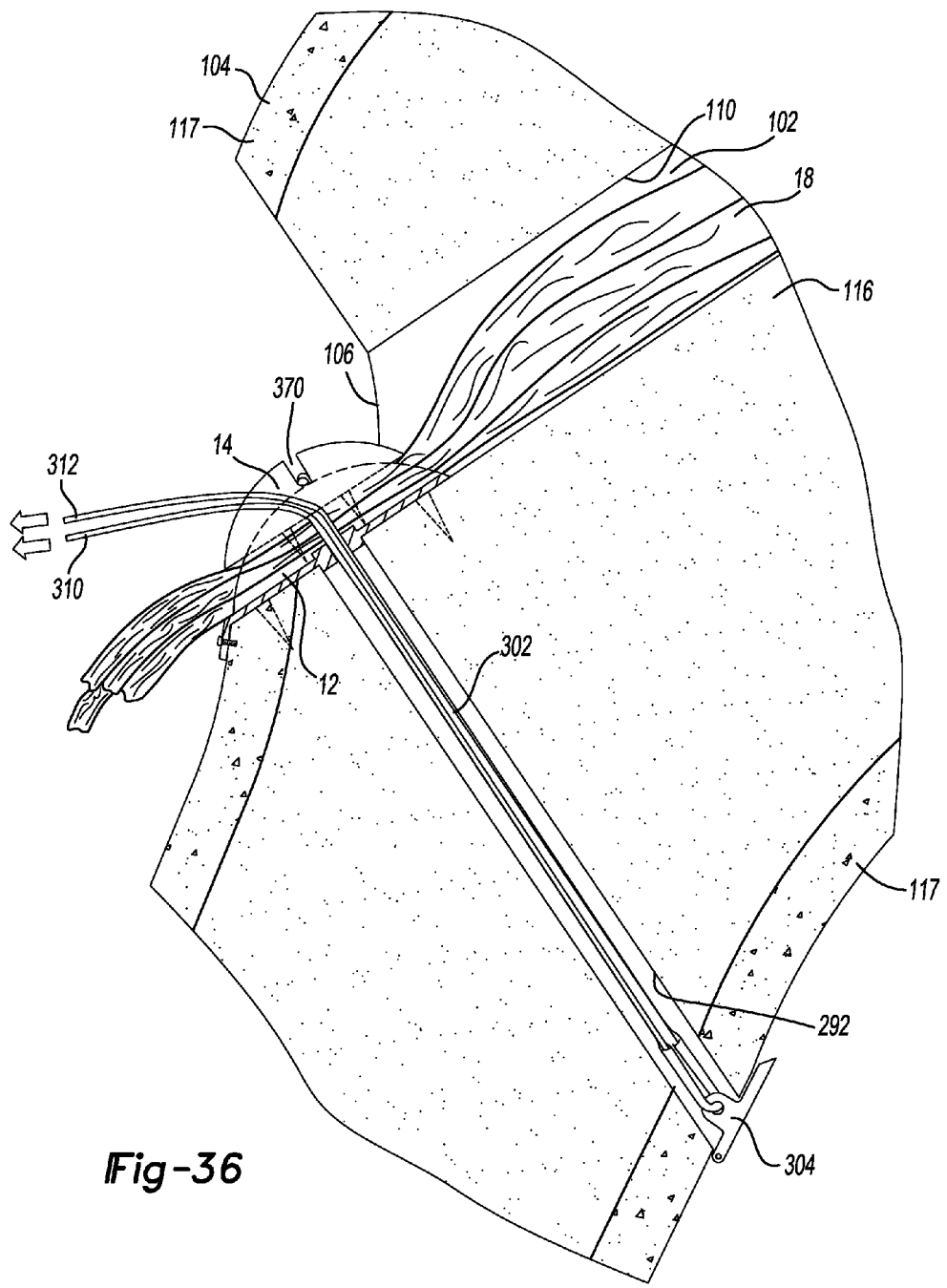

FIG. 29 further illustrates the graft fixation assembly including the compression member of FIG. 27 being implanted into a tibia bone;

FIG. 30 still further illustrates the graft fixation assembly including the compression member of FIG. 27 being implanted into a tibia bone;

FIG. 31 illustrates another graft fixation assembly according to the present teachings being implanted into a tibia bone;

FIG. 32 further illustrates the graft fixation assembly of FIG. 31 according to the present teachings being implanted into a tibia bone; and FIGS. 33-36 illustrate another method of implanting a graft fixation assembly according to the present teachings into a tibia bone.

Corresponding reference numerals indicate corresponding parts throughout the several views of the drawings.

DETAILED DESCRIPTION

Example embodiments will now be described more fully with reference to the accompanying drawings. It should be noted that while an ACL soft tissue graft and tibial tunnel are illustrated herein, such a use is merely exemplary and other soft tissue repair and other bone tunnels can be employed.

Figure 1:
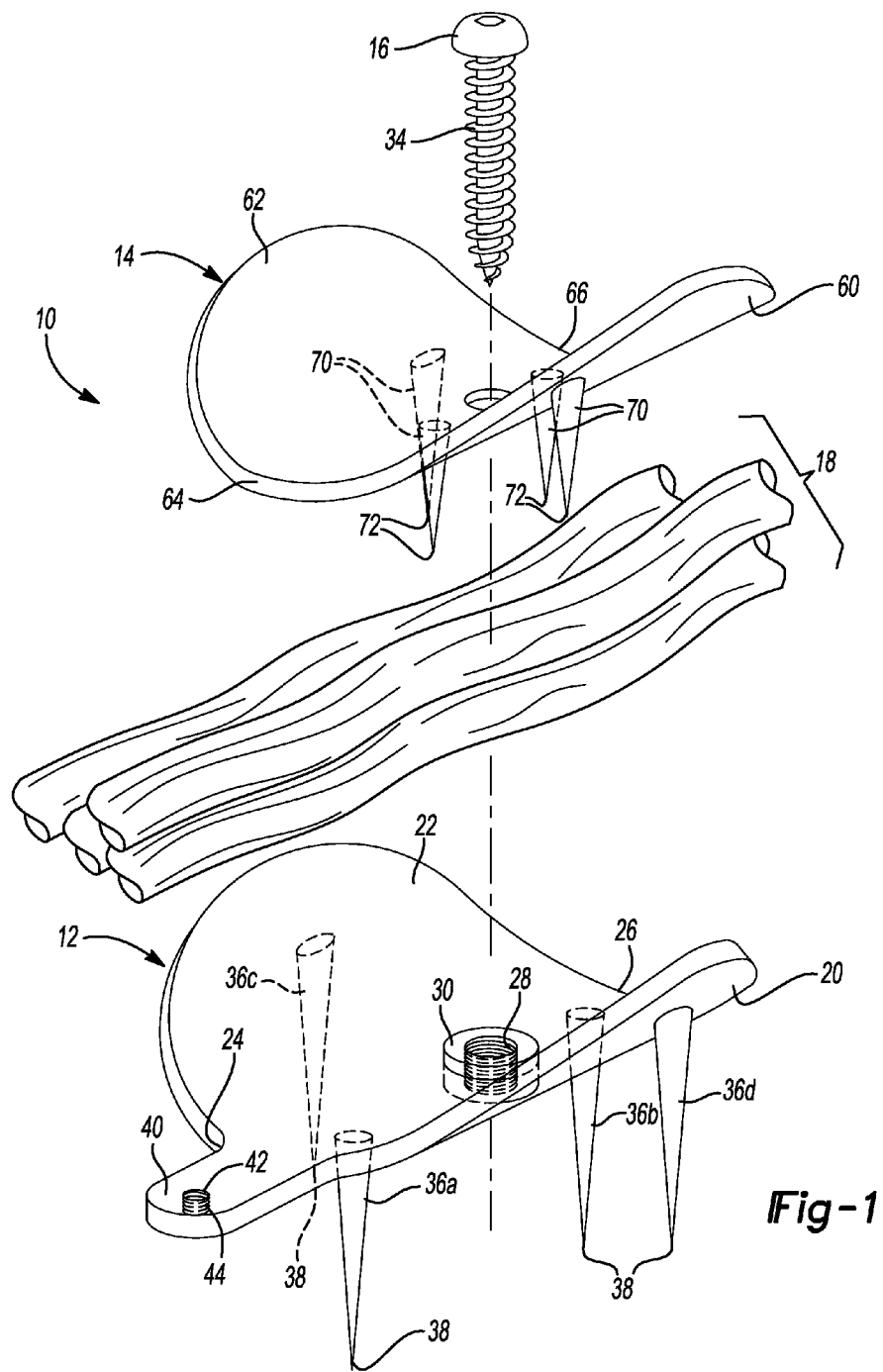
FIG. 1 is an exploded view of a graft fixation assembly according to the present teachings.

With initial reference to FIG. 1, a graft fixation assembly according to the present teachings is illustrated at reference numeral 10. The graft fixation assembly 10 generally includes a base member 12 and a complementary compression member 14, which can be secured together with a coupling member, such as a fastener 16. A soft tissue graft 18, such as an ACL graft, can be compressed between the base member 12 and the compression member 14 to anchor and fix the graft 18 at a desired location, such as within a tibial tunnel, as further described herein.

With continued reference to FIG. 1 and additional reference to FIGS. 2-4, the base member 12 generally includes a convex bone engaging surface 20, a concave graft engaging surface 22, a first end 24, and a second end 26. The convex bone engaging surface 20 is opposite to the concave graft engaging surface 22 and the first end 24 is opposite to the second end 26. A first longitudinal axis A (FIG. 4) extends from the first end 24 to the second end 26 parallel to both an apex of the convex bone engaging surface 20 and a bottom of the concave graft engaging surface 22. The base member 12 is generally shaped such that it can sit flush against an inner surface of a circular bone tunnel, such as a tibial tunnel, as further described herein. Therefore, the base member 12 has a constant cross-sectional radius R (FIG. 2), which corresponds to the tunnel radius. The base member 12 is sized such that when implanted or nested in a posterior surface of the tibial tunnel, the base member 12 does not cross a plane extending along a longitudinal axis of the tunnel separating the tunnel into an anterior half and a posterior half.

The base member 12 defines a first central aperture 28 extending between the convex bone engaging surface 20 and the concave graft engaging surface 22. The first aperture 28 is aligned along the first longitudinal axis A about half way between the first end 24 and the second end 26. The first aperture 28 extends through the first longitudinal axis A along an axis that is generally perpendicular to the first longitudinal axis A. The first aperture 28 is sized and shaped to receive a coupling member, such as the fastener 16, for example.

The first aperture 28 can be defined by a base housing 30, which can extend beyond one or both of the convex bone engaging surface 20 and the concave graft engaging surface 22. The base housing 30 can also be flush with one or both of the convex bone engaging surface 20 and the concave graft engaging surface 22. The first aperture 28 can include first aperture threads 32 configured to cooperate with first fastener threads 34 of the fastener 16.

A plurality of first fixation members 36 extend from the convex bone engaging surface 20. Each of the first fixation members 36 include a spike orientated such that a largest diameter portion of each first fixation member 36 is at the convex bone engaging surface 20. Each first fixation member 36 generally tapers to a pointed tip 38 at an end that is opposite to the convex bone engaging surface 20. The first fixation members 36 can be integral with the convex bone engaging surface 20 or modular.

Any suitable number of first fixation members 36 can be provided and arranged at any suitable location at the convex bone engaging surface 20 in order to adequately secure the base member 12 in bone. As illustrated in FIGS. 1-4 for example, the base member 12 includes four first fixation members 36a-36d. Two of the first fixation members 36a and 36b are arranged along the first longitudinal axis A on opposite sides of the first aperture 28. Two additional fixation members 36c and 36d are arranged on opposite sides of the first aperture 28 along a first line B that intersects the first longitudinal axis A at the first aperture 28, is perpendicular to the first longitudinal axis A, and generally follows the overall curvature of the base member 12.

As illustrated in FIG. 2A, the base member 12 may also include a plurality of graft fixation members 37 extending from the concave graft engaging surface 22 to engage the graft 18 and further secure the graft 18 between the base member 12 and the compression member 14. The graft fixation members 37 are generally shorter than the first fixation members 36 and may be arranged at any suitable location on the concave graft engaging surface 22 in any suitable number.

Figure 8:
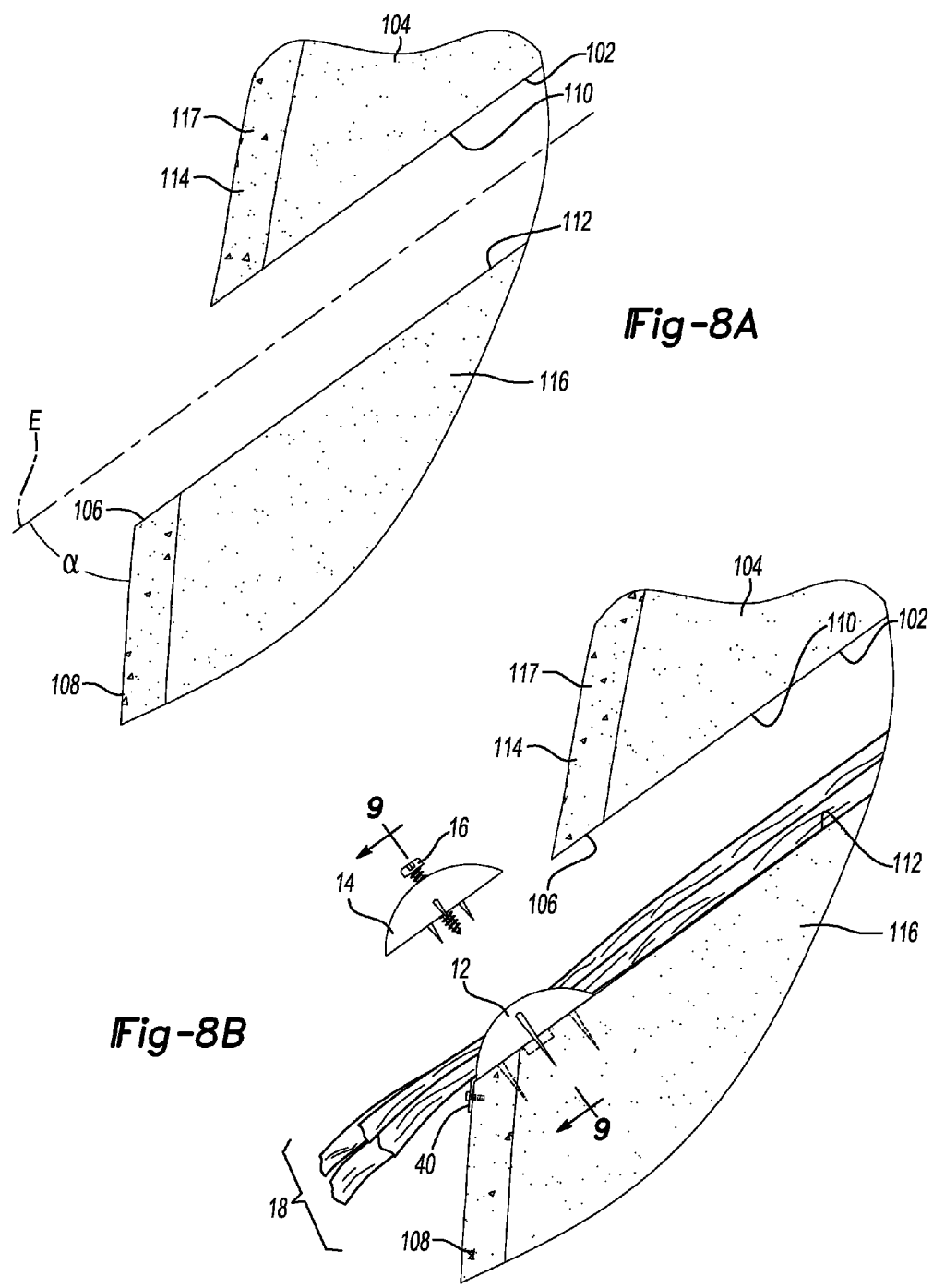
FIG. 8A is a cross-sectional view of an exemplary tibial tunnel formed in a tibia bone.
FIG. 8B is a cross-sectional view of the tibial tunnel and a side view of the graft fixation assembly of FIG. 1.

The base member 12 further may include a rigid flange 40 extending from the first end 24 at an angle to the first longitudinal axis A. The flange 40 may also define a flange aperture 42. The flange aperture 42 may include threads 44 and is configured to receive a suitable fastener to further secure the base member 12 to bone. The flange 40 can instead be flexible to facilitate positioning of the flange 40 against bone, such as at an outer surface of a tibia bone proximate to a tibia tunnel, as illustrated in FIG. 8B for example and further described herein. The compression member 14 may also possess a flange similar to the flange 40.

Figure 5:
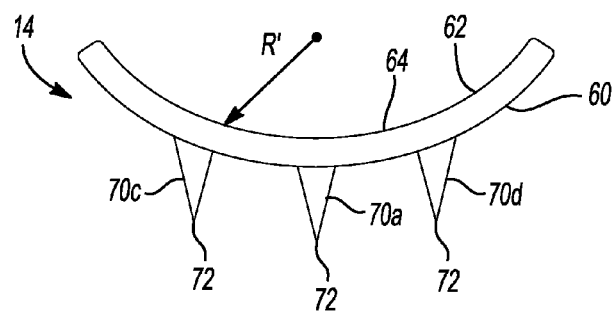
FIG. 5 is a front view of a compression member of the graft fixation assembly of FIG. 1.
Figure 6:
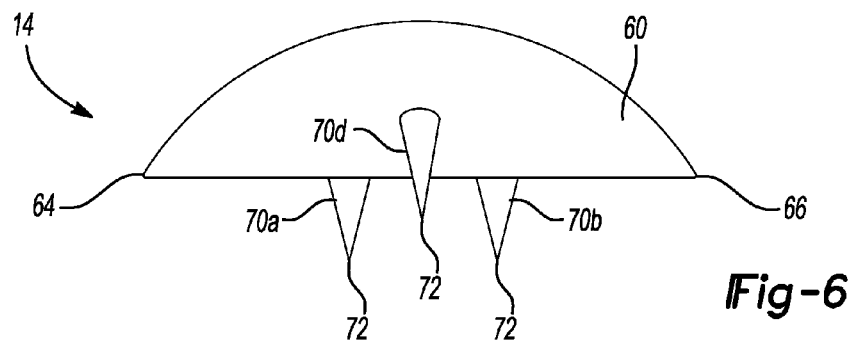
FIG. 6 is a side view of the compression member of the graft fixation assembly of FIG. 1.
Figure 7:
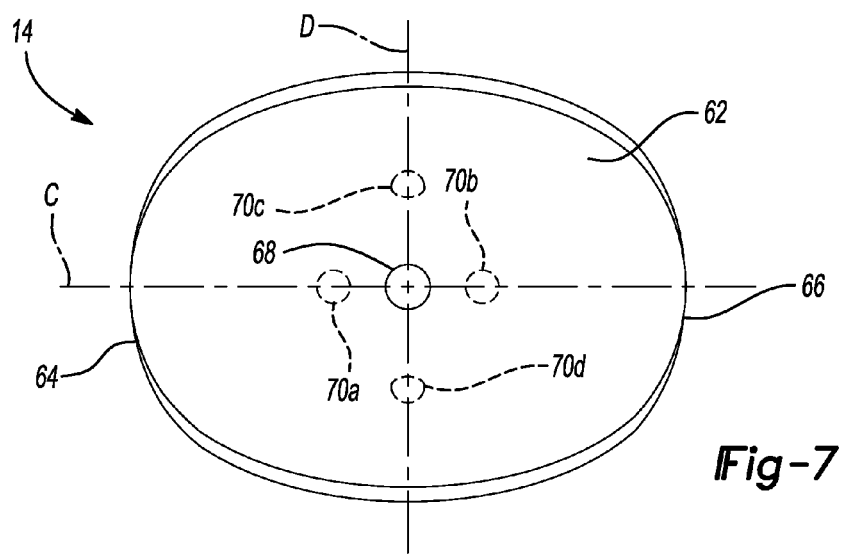
FIG. 7 is a top view of the compression member of the graft fixation assembly of FIG. 1.

With continued reference to FIG. 1 and additional reference to FIGS. 5-7, the compression member 14 generally includes a convex graft engaging surface 60, a concave outer surface 62, a first end 64, and a second end 66. The convex graft engaging surface 60 is opposite to the concave outer surface 62 and has a radius R', which is complementary to the radius R of the concave graft engaging surface 22 of the base member 12. A second longitudinal axis C extends from the first end 64 to the second end 66 parallel to both an apex of the convex graft engaging surface 60 and a base of the concave outer surface 62. The graft engaging surfaces 22 and 60 can be smooth or rough with a texture to enhance fixation of the graft 18 therebetween.

The compression member 14 defines a second aperture 68 extending between the convex graft engaging surface 60 and the concave outer surface 62. The second aperture 68 is aligned along the second longitudinal axis C, is about equidistant between the first end 64 and the second end 66, and extends along an axis that is substantially perpendicular to the second longitudinal axis C. The second aperture 68 may alternatively be biased more in the anterior direction to affect the compression profile on the graft. The second aperture 68 is sized and shaped to receive a suitable coupling member, such as the fastener 16, and may or may not be threaded.

Figure 11:
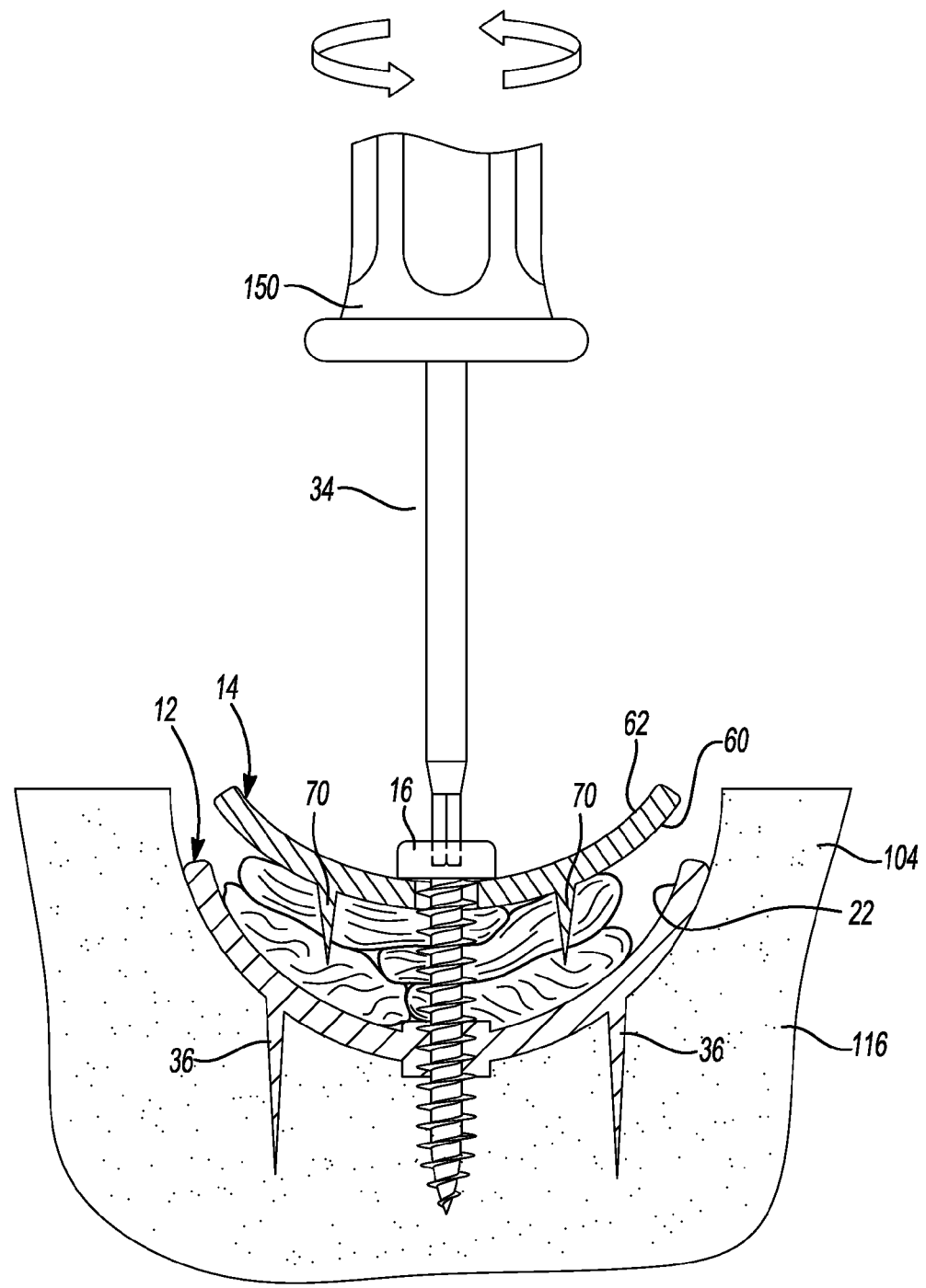
FIG. 11 is a cross-sectional view of the compression member of the graft fixation assembly being connected to the base member of the graft fixation assembly of FIG. 1.

Extending from the convex graft engaging surface are a plurality of second fixation members 70, each of which are tapered and terminate at a pointed tip 72. A first pair of the second fixation members 70a and 70b are arranged along the second longitudinal axis C on opposite sides of the second aperture 68. A second pair of the second fixation members 70c and 70d are also arranged on opposite sides of the second aperture 68, along a second line D that is about perpendicular to the second longitudinal axis C and generally follows the overall curvature of the compression member 14. Each of the second fixation members 70 have a length to generally only engage the graft 18 and not extend to the base member 12 when the graft 18 is compressed between the compression member 14 and the base member 12, as illustrated in FIG. 11 for example. The second fixation members 70 may alternatively be provided with an increased length such that the fixation members 70 extend to the base member 12.

The compression member 14 is shaped and sized to be generally complementary to the base member 12. As such, the convex graft engaging surface 60 has a radius of curvature that is substantially similar to a radius of curvature of the concave graft engaging surface 22, as illustrated in the cross-sectional view of FIG. 9 for example. However, the convex graft engaging surface 60 and the concave graft engaging surface 22 need not have similar curvatures. For example, the convex graft engaging surface 60 may be substantially planar. The graft engaging surface 22 may also flex to engage more thoroughly with the graft 18 and the base plate 12.

The base member 12 and the compression member 14 can be made of any suitable biocompatible material. For example, the base member 12 and the compression member 14 can each include any one or more of titanium, stainless steel, polyether ether ketone ("PEEK"), or LACTOSORB®. LACTOSORB® is an absorbable co-polymer synthesized from all-natural ingredients: 82% L-lactic acid and 18% glycolic acid, and is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of its strength for a time period that is appropriate for healing, but not so long as to raise concerns about long-term stress shielding of bone. In addition to LACTOSORB®, other resorbable materials may be used such as PLA, PGA, and others including various polymers, ceramics, etc. The base member 12 and the compression member 14 can each be substantially rigid or flexible. The base member 12 may more readily conform to the bone surface against which it is implanted when made from a flexible material.

With additional reference to FIGS. 8-11, a method for tibial fixation of the soft tissue graft 18 will now be described. Initially, soft tissue grafts are harvested for use in an anterior cruciate ligament (ACL) reconstruction. The semitendinosus and gracilis tendons from their respective hamstring muscles are generally used and harvested from the patient or by way of donor tendons using techniques known in the art. Alternatively synthetic grafts may also be employed. The harvested grafts will generally include two tubular grafts that are subsequently looped at their mid-section to form a four bundle graft. The four bundle graft should be sized to pass without friction through a tibial and femoral tunnel.

Once the grafts have been harvested and prepared using known techniques, a tunnel or hole placement is performed. With reference to FIG. 8A for example, a tibial tunnel or bore 102 is drilled through tibia 104 and into the femur (not shown). The tibial tunnel 102 is provided with a diameter between about 7 to about 13 millimeters, such as between about 8 to about 9 millimeters, and is bored using a drill bit and a driver. The tibial tunnel 102 exits at about a center of the tibial plateau and enters the tibia 104 at about 50 millimeters from the top of the tibial plateau medial to the tibial tubercle or at the medial cortex. Because the tibial tunnel 102 extends through the tibia 104 at an angle, it creates an elliptical entrance opening 106 at an anterior exterior surface 108 of the tibia 104 and an elliptical exit opening (not shown). The tibial tunnel 102 includes an anterior wall surface 110 and a posterior wall surface 112 opposite to the anterior wall surface 110.

Because the tibial tunnel 102 is angled through the tibia 104 and is not perpendicular to the anterior exterior surface 108, the posterior wall surface 112 extends beyond the anterior wall surface 110 such that the anterior wall surface 110 does not overlap the posterior wall surface 112 at the entrance opening 106. With reference to both FIG. 8A and FIG. 8B, the size of the entrance opening 106 and the degree to which the anterior wall surface 110 overlaps the posterior wall surface 112 at the entrance opening 106 depends on the angle at which the tibial tunnel 102 intersects the anterior exterior surface 108. For example, if the tibial tunnel 102 is formed such that a tunnel longitudinal axis E is at an angle $\alpha$ relative to the exterior surface 108 that is less than about 45°, as illustrated in FIGS. 8A and 8B, then the entrance opening 106 will likely be large enough to receive the graft fixation assembly 10 without removing additional portions of the tibia 104. However, if the angle $\alpha$ is greater than about 45° and the entrance opening 106 is too small to accommodate the graft fixation assembly 10, then an anterior edge 114 of the tibia 104 may have to be removed at the entrance opening 106 to enlarge the entrance opening 106, as further described herein.

The base member 12 is implanted first. The base member 12 is implanted into the posterior wall surface 112 of the tibial tunnel 102 perpendicular to the tunnel longitudinal axis E in any suitable manner, such as by impaction with an impactor. The base member 12 is impacted such that the first fixation members 36 are driven into the posterior wall surface 112 and cancellous bone 116 below. The convex bone engaging surface 20 abuts the posterior wall surface 112. If the base member 12 includes a base housing 30 that extends from the convex bone engaging surface 20, then the base member 12 is also impacted into the posterior wall surface 112. The remainder of the base member 12, including the concave graft engaging surface 22, extends within the tibial tunnel 102.

To further secure the base member 12 at the entrance opening 106 and prevent the base member 12 from moving in the tibial tunnel 102, the flange 40 can be bent and placed in contact with the anterior exterior surface 108. A suitable fastener can be inserted through the flange aperture 42 and into the exterior surface 108. Securing the tab flange 40 with a fastener is optional, as is the flange 40 itself. After the base member 12 is mounted to the posterior wall surface 112 of the tibial tunnel 102, the soft tissue graft 18 is positioned within the tibial tunnel 102 and secured to the femur as known in the art and as described in U.S. Pat. No. 7,211,111 for example (assigned to Biomet Sports Medicine, Inc. of Warsaw, Ind.), the teachings of which are incorporated herein by reference.

The graft 18 is orientated such that it extends across and is seated on the concave graft engaging surface 22. The graft 18 is tensioned generally by means of pulling on opposite ends of the graft 18 manually or with a tensioning device. An exemplary tensioning device is set forth in U.S. Pat. No. 5,507,750 titled "Method and Apparatus for Tensioning Grafts and Ligaments," which is hereby incorporated by reference.

Figure 10:
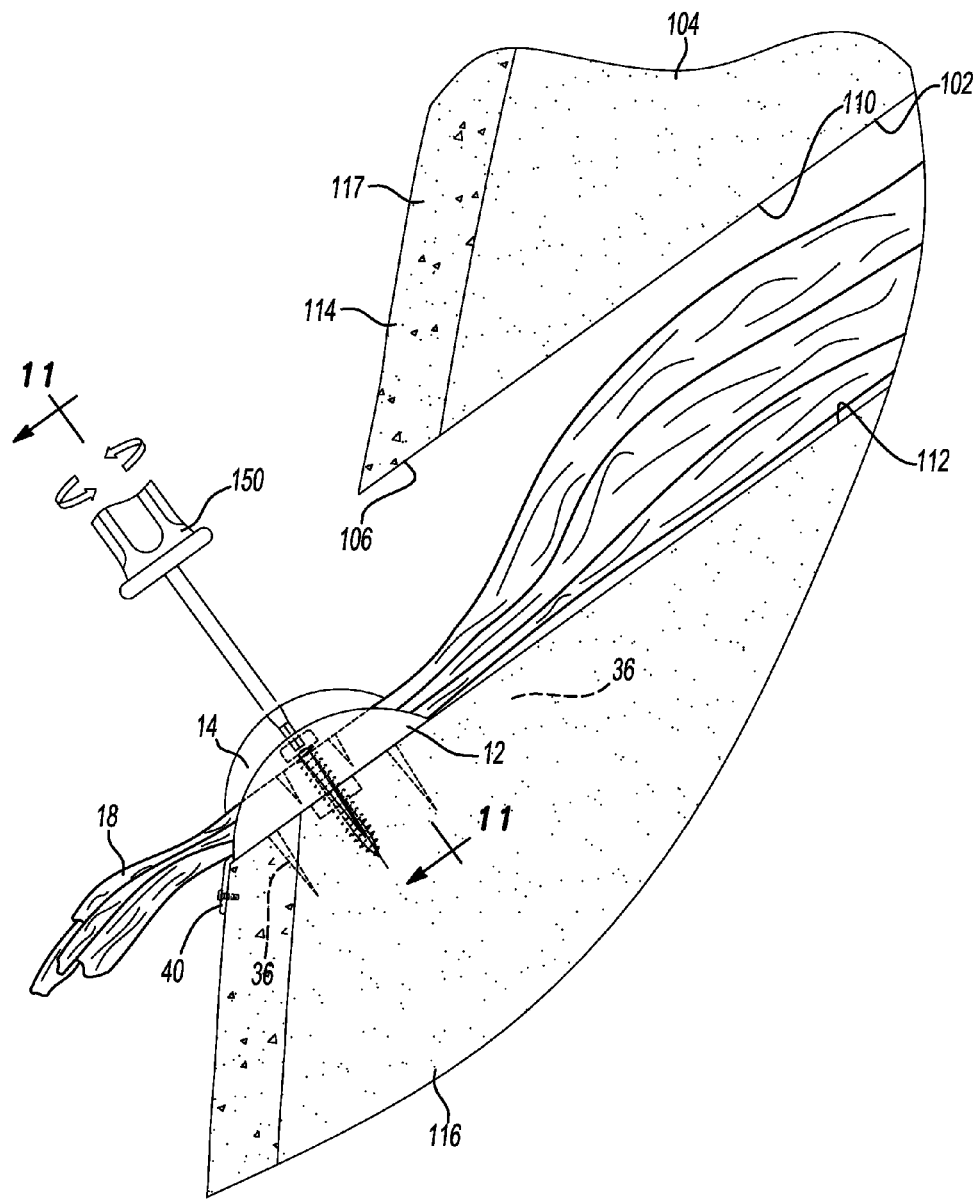
FIG. 10 is a cross-sectional view of the tibial tunnel with the graft fixation assembly of FIG. 1 being implanted therein.

Once the proper tension of the soft tissue graft 18 is achieved, the compression member 14 is placed over the soft tissue graft 18 such that the convex graft engaging surface 60 contacts the graft 18 and the second fixation members penetrate the graft. The fastener 16 is inserted through or between fibers of the soft tissue graft 18 and brought into cooperation with the first aperture 28 of the base member 12. Using a screw driver 150 or other suitable device, the fastener 16 is rotated and driven further into the first aperture 28, thereby drawing the compression member 14 towards the base member 12 and compressing the soft tissue graft 18 therebetween to secure the graft 18 to the graft fixation assembly 10. As a result, the graft 18 is anchored at the entrance opening 106 with the graft fixation assembly 10. As illustrated in FIGS. 10 and 11, the fastener 16 can be driven through the base member 12 and into the cancellous bone 116. The fastener 16 can be sized such that it either extends only into the cancellous bone 116 or terminates in the opposite bone cortex 117. Alternatively, the fastener 16 can be sized such that it does not penetrate the bone 104 at all. The fastener 16 can be self-tapping, to avoid the need to drill a bore in the tibia 104. The fastener 16 need not be a screw, and any other suitable fastening device or technique may be used. The graft 18 can be anchored in the femur using any suitable fastening device and/or technique.

Because of the shape and size of the entrance opening 106 illustrated in FIGS. 8A, 8B, and 10 for example, there is no need to remove additional portions of the tibia bone 104, such as at the anterior edge 114, in order to implant the graft fixation assembly 10, which is desirable to maintain more of the anterior tibia bone 104.

Due to the anatomy of a patient's tibia and/or the size and shape of the entrance opening 106, there may be a need to enlarge the entrance opening 106 by removing a portion of the anterior edge 114 of the tibia 104. A cutting device 202, as illustrated in FIGS. 12-15, is thus provided. The cutting device 202 can be used to increase the size of the entrance opening 106 by cutting surrounding portions of tibia bone, specifically the anterior edge 114 of tibia 104. The cutting device 202 can also be used to cut any other suitable bone surface.

The cutting device 202 generally includes a main body 204 having a first end 206 and a second end 208 that is opposite to the first end 206. At the first end 206 is a first sidewall 210, which includes a curved cutting blade 212. Extending from each end of the curved cutting blade 212 are elongated cutting edges 214a and 214b. Each of the cutting edges 214a and 214b are generally planar and extend from the curved cutting blade 212.

The cutting device 202 further includes an inner wall 220 between the first end 206 and the second end 208. The main body 204 defines a cutting clearance 222 between the first sidewall 210 and the inner wall 220 to accommodate bone being cut with the cutting device 202, as further described herein. Extending from an anterior surface 224 of the main body 204 between the first sidewall 210 and the inner wall 220, in the region of the cutting clearance 222, is a knob 226. The knob 226 includes any suitable size and shape to permit coupling with a suitable driver or impaction device to drive the cutting device against bone to be cut, as further described herein.

The main body 204 defines a pair of locator receptacles 230a and 230b between the inner wall 220 and the second end 208. Each of the locator receptacles 230a and 230b extend through the main body 204 generally parallel to one another. The locator receptacles 230a and 230b each extend parallel to the first sidewall 210 and the cutting blade 212. The locator receptacles 230a and 230b are generally cylindrical, but may be of any suitable shape or configuration to mate with locator features of, for example, a guide pin.

With additional reference to FIGS. 16 and 17, a guide pin is generally illustrated at reference numeral 250. The guide pin 250 is generally shaped as a cylindrical rod that includes a distal end 252 and a proximal end 254. The distal end 252 and the proximal end 254 are at opposite ends of the guide pin 250. The guide pin 250 further includes first and second locator pins 256a and 256b, a stabilizing pin 258, and a guide bore 260.

The locator pins 256 and the stabilizing pin 258 extend from opposite sides of the guide 250. The locator pins 256a and 256b are generally parallel cylindrical rods sized and shaped such that the first locator pin 256a can be received within the first locator receptacle 230a and the second locator pin 256b can be received within the second locator receptacle 230b. The guide bore 260 is defined by a body 262 of the guide pin 250 and extends generally parallel to each of the locator pins 256 and the stabilizing pin 258. The guide bore 260 is sized and shaped to accommodate a suitable cutting device, such as a drill bit, as further described herein.

The locator pins 256 and the stabilizing pin 258 are arranged along the body 262 such that upon insertion of the distal end 252 within the tibial tunnel 102, contact between the stabilizing pin 258 and the exterior surface 108 of the tibia 104 will place the locator pins 256 in position to support the cutting device 202 at a desired portion of bone to be cut. The locator pins 256 and stabilizing pin 258 can be located at any suitable position along the body 262 to locate the cutting device 202 at bone to be cut.

With additional reference to FIGS. 18-21, use of the cutting device 202 and the guide pin 250 to increase the size of the entrance opening 106 by removing a portion of the anterior edge 114 of the tibia 104 will now be described. As discussed above, it can be desirable or necessary to increase the size of the entrance opening 106 when the anterior edge 114 and anterior wall surface 110 overlap enough of the posterior wall surface 112 of the tibial tunnel 102 such that it is difficult or not possible to mount the base member 12 to the posterior wall surface 112 or attach the compression member 14 thereto.

Figure 18:
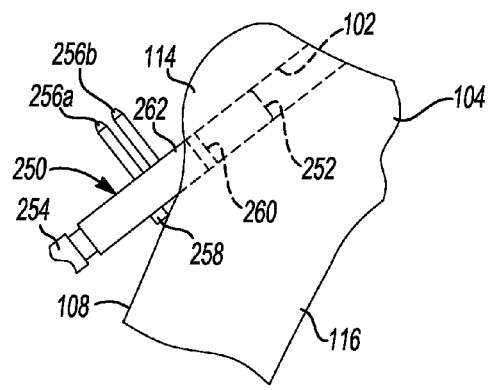
FIG. 18 is a side view of the guide pin inserted into an exemplary tibial tunnel formed in a tibia.

As illustrated in FIG. 18, after the tibial tunnel 102 is formed in the tibia 104, the distal end 252 of the guide pin 250 is inserted through the entrance opening 106 into the tibial tunnel 102 until the stabilizing pin 258 abuts the exterior surface 108 of the tibia 104. The cutting device 202 is mated with the guide pin 250 by inserting the locator pins 256a and 256b into the locator receptacles 230a and 230b respectively.

Figure 19:
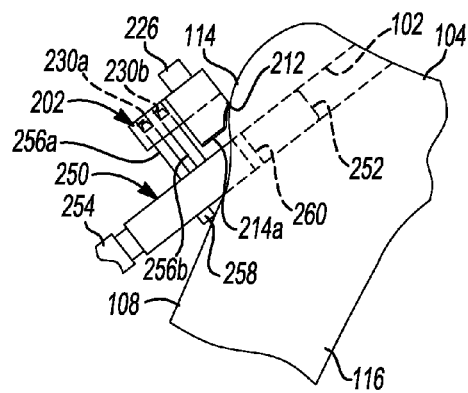
FIG. 19 is a side view of the cutting device in cooperation with the guide pin to cut an anterior edge of the tibia.

Mating the cutting device 202 with the guide pin 250 positions the cutting blade 212 at a surface of the anterior edge 114 to be cut, as illustrated in FIG. 19. Thus, if a greater portion of the anterior edge 114 is desired to be cut, the guide pin 250 can be provided with the stabilizing pin 258 closer to the proximal end 254, thus allowing the guide pin 250 to extend further into the tibial tunnel 102. If less of the anterior edge 114 is desired to be cut, the stabilizing pin 258 can be provided closer to the distal end 252, thereby restricting the distance that the guide pin 250 extends into the tibial tunnel 102. The pins 256a, 256b, and 258 can thus be adjustable by being movable along a length of the guide pin 250.

Figure 20:
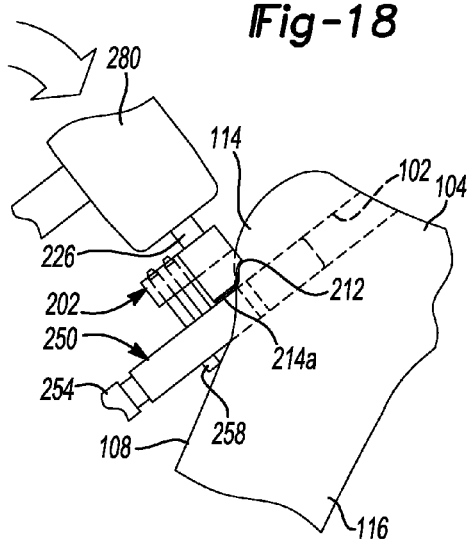
FIG. 20 is a side view of the cutting device cutting the anterior edge of the tibia.
Figure 21:
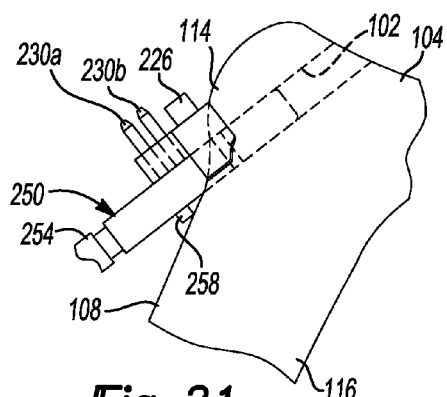
FIG. 21 is a side view of the cutting device further cutting the anterior edge of the tibia.

As illustrated in FIGS. 20 and 21, after the cutting device 202 is located at a desired portion of the anterior edge 114 of the tibia 104, the cutting device 202 is impacted with a suitable impaction device, such as a hammer 280 at the knob 226 to drive the curved cutting blade 212 and the cutting edges 214a and 214b into the anterior edge 114 of the tibia 104 to cut through the tibia 104 and remove the anterior edge 114. The cutting clearance 222 between the first sidewall 210 and the inner wall 220 accommodates the portion of the anterior edge 114 that the cutting device 202 is impacted over.

Removing the anterior edge 114 and a portion of the anterior wall surface 110 increases the size of the entrance opening 106, provides greater access to both the tibial tunnel 102 and the anterior wall surface 110, and facilitates implantation of the graft fixation assembly 10 in the tibial tunnel 102 generally along an axis that is perpendicular to the tunnel longitudinal axis E while permitting the posterior wall surface 112 to remain intact.

Figure 22:
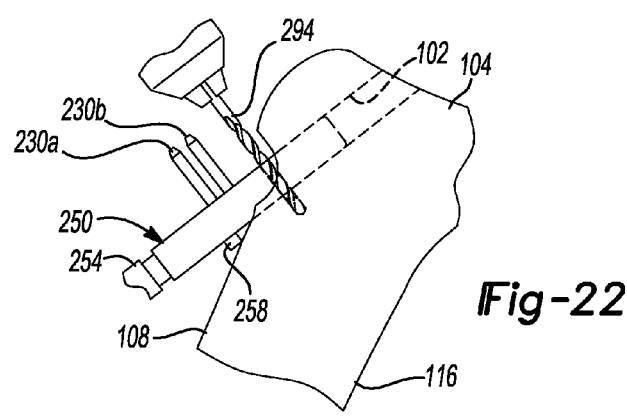
FIG. 22 is a side view of a bore being formed in the tibia using the guide pin as a guide.
Figure 23:
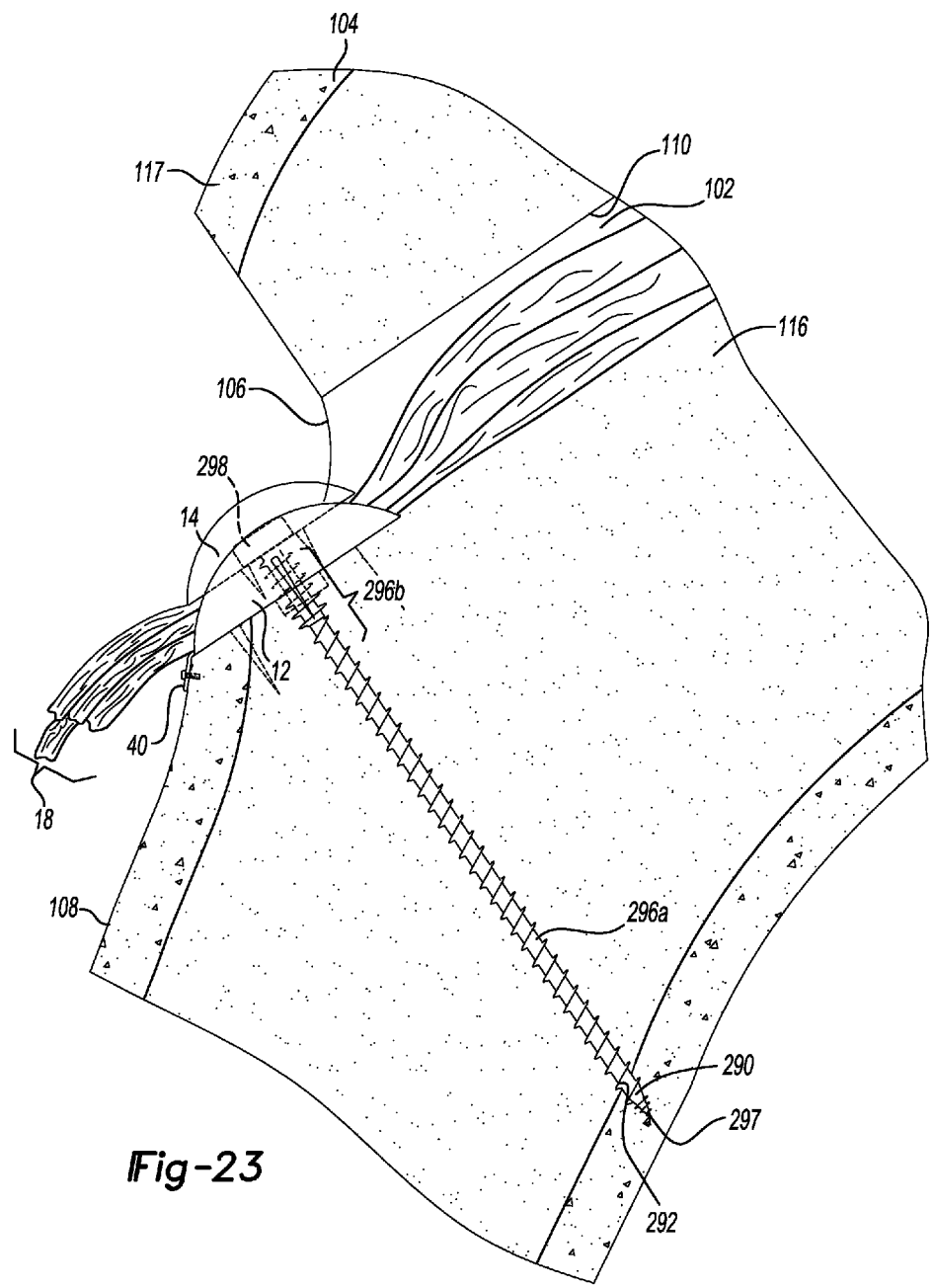
FIG. 23 is a cross-sectional view of the graft fixation assembly secured in the tibia tunnel with a bicortical screw.

With additional reference to FIGS. 22 and 23, the compression member 14 can be coupled to the base member 12 with an elongated bicortical screw 290 (FIG. 23). The bicortical screw 290 can be self-tapping and can be inserted in a bore 292 formed through the tibia bone 104 to extend from a posterior side of the bone tunnel, through cancellous bone 116, to the opposite cortex 117. As illustrated in FIG. 22, the bore 292 can be formed using the guide pin 250. With the guide pin 250 inserted within the tibial tunnel 102, a suitable cutting device, such as a drill bit 294 of a drill can be inserted through the guide bore 260 and driven into the bone 104 (cancellous or posterior wall of the tibial tunnel 102) to form the bore 292. While the bore 292 is illustrated in FIG. 22 as being formed in conjunction with use of the cutting device 202 to remove the anterior edge 114 of the tibia 104, the bore 292 can be formed without using the cutting device 202 where the size and shape of the opening 106 is sufficient to accommodate the drill bit 294.

As illustrated in FIG. 23, the bicortical screw 290 is positioned in a manner similar to the fastener 16 to secure the compression member 14 to the base member 12 and compress the graft 18 therebetween. Unlike the fastener 16, the bicortical screw 290 extends to the opposite side of the bone cortex 117 through cancellous bone 116 therebetween. The bicortical screw may include a plurality of first threads 296a, a plurality of second threads 296b, a tip 297, and a head 298. The threads 296a can be configured to optimize engagement with the cancellous bone 116, the cortical bone 117, and the compression member 14. The first threads 296a may also have a smaller diameter than the second threads 296b and the first aperture 28 of the base member 12 to permit the first threads 296a to pass through the first aperture 28 easily. The first and second threads 296a and 296b can also be uniform.

Figure 24:
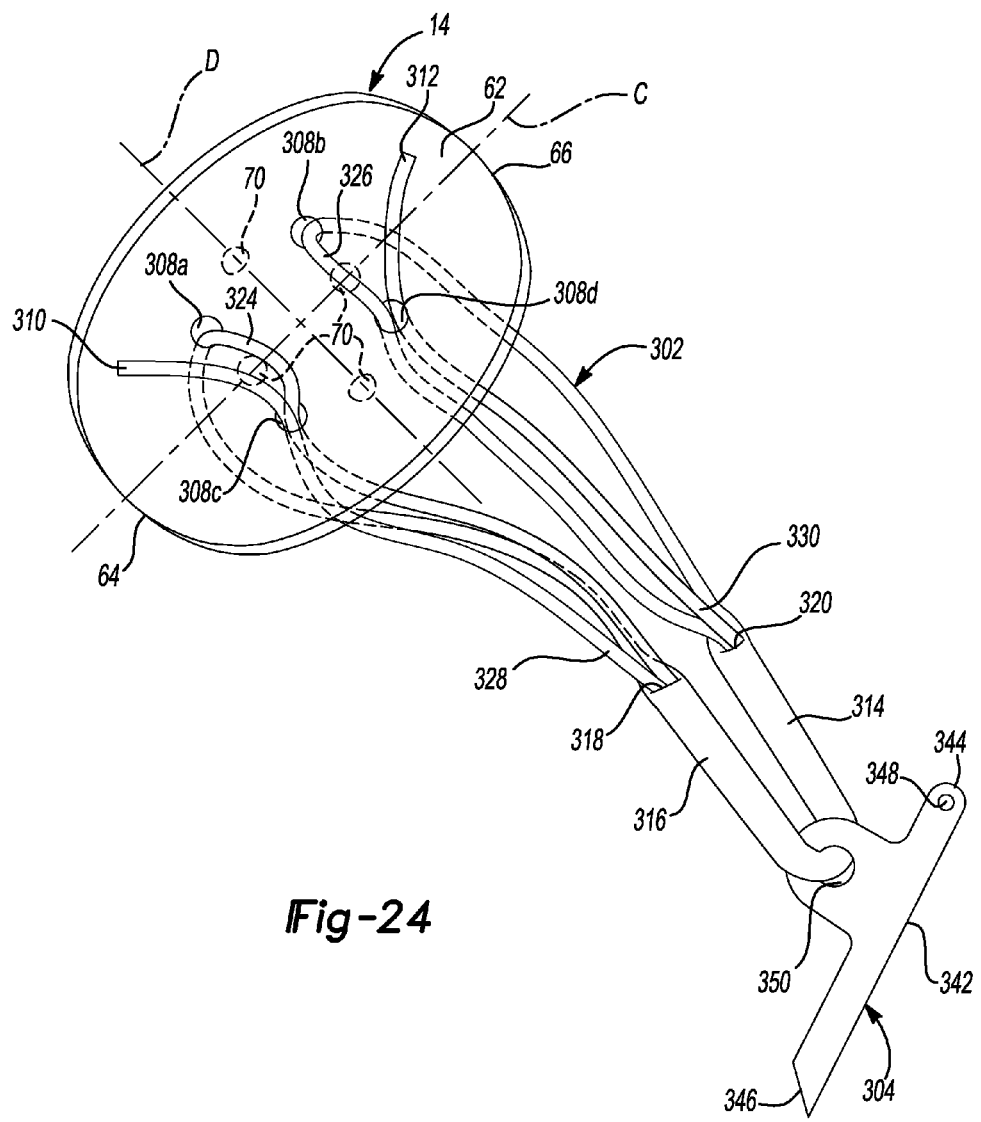
FIG. 24 illustrates a compression member of the graft fixation assembly with a self-locking suture construct connected thereto.
Figure 25:
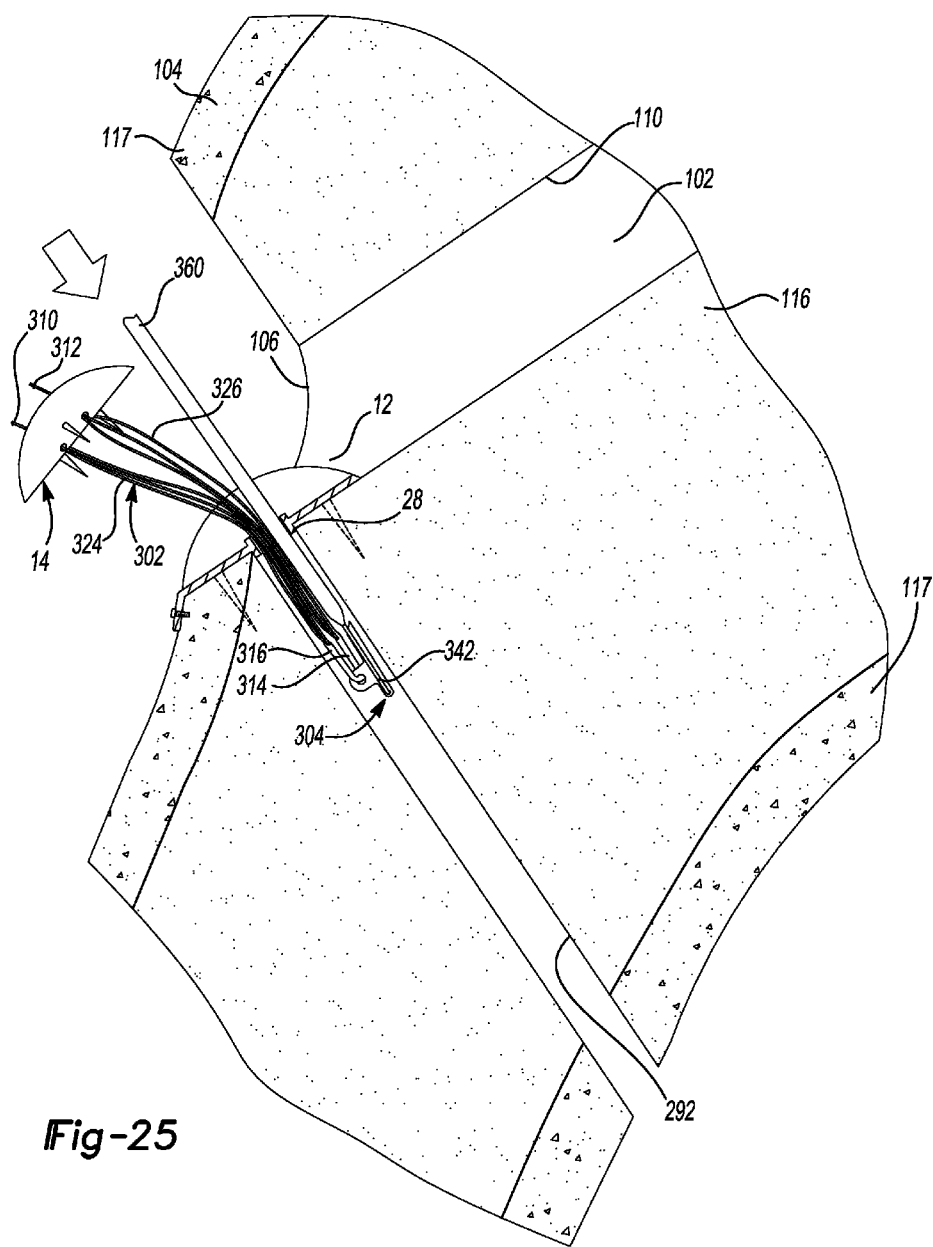
FIG. 25 illustrates the compression member of FIG. 24 being mounted to a tibia bone.
Figure 26:
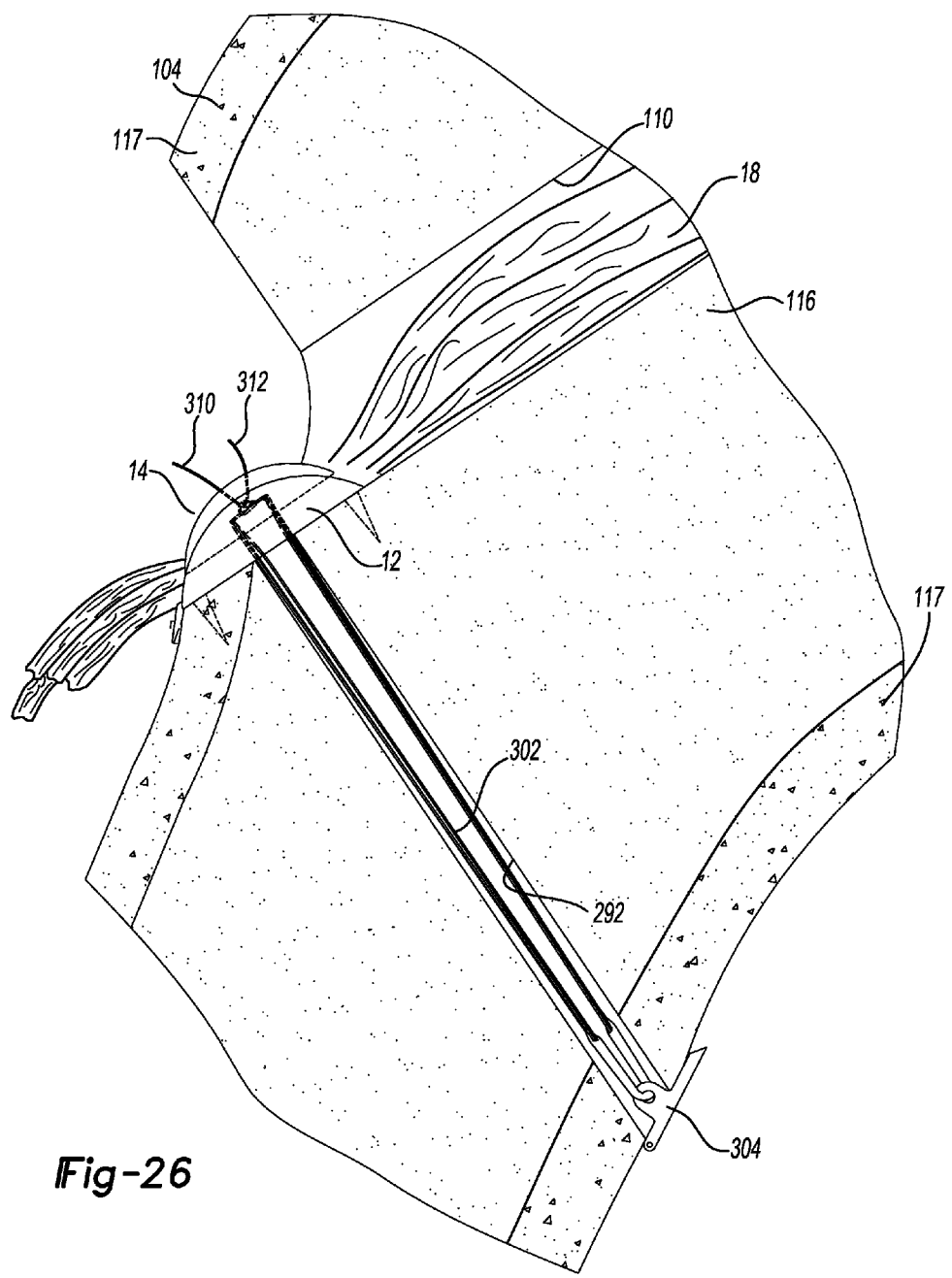
FIG. 26 illustrates the compression member of FIG. 24 mounted to the tibia bone with a graft compressed between the compression member and a base member of the graft fixation assembly.

With reference to FIGS. 24-26, the compression member 14 can be compressed against the soft tissue graft 18 and the base member 12 with a knotless, self-locking suture construct 302 anchored at an opposite side of the bone cortex 117 with an anchor 304, such as a ToggleLoc™ or EZLoc™ by Biomet of Warsaw, Ind.

To accommodate the suture construct 302, the compression member 14 includes, in place of the second aperture 68, a first suture aperture 308a, a second suture aperture 308b, a third suture aperture 308c, and a fourth suture aperture 308d. The suture apertures 308a-308d are equally spaced apart with the first and second suture apertures 308a and 308b on an opposite side of the second longitudinal axis C than the third and fourth suture apertures 308c and 308d.

The suture construct 302 generally includes a first end 310 and a second end 312. The suture construct 302 is formed of a braided body 314 that defines a longitudinal passage formed therein. First and second apertures 318 and 320 are defined in or through the braided body 322 at opposite ends of a sleeve portion 316. The first end 310 of the suture is passed through the second aperture 320 into the passage and through the sleeve portion 316, and extends out from the first aperture 318. The second end 312 is passed through the first aperture 318 into the passage, through the sleeve portion 316, and out through the second aperture 320. As a result, two adjustable loops 324 and 326 are formed. The longitudinal and parallel placement of first and second suture portions 328 and 330 of the suture construct 302 within the sleeve portion 316 resists reverse relative movement of the first and the second suture portions 328 and 330 of the suture construct 302 once it is tightened.

The suture construct 302 is self-locking such that as the first and the second ends 310 and 312 are pulled, friction between the interior of the sleeve portion 316 and the first and second suture portions 328 and 330 located within the sleeve portion 316 causes the suture construct 302 to "automatically" lock in a reduced size or diameter configuration in which tension is maintained without use of a knot. The suture construct 302 is similar to the self-locking suture construct 300A of FIG. 15 of U.S. application Ser. No. 12/915,962 filed on Oct. 29, 2010, titled Method and Apparatus for Securing Soft Tissue to Bone, and assigned to Biomet Sports Medicine, LLC, the disclosure of which is incorporated herein by reference. Additional description of the suture construct 302 is thus included in U.S. application Ser. No. 12/915,962. Additional exemplary sutures that can be used in accordance with the present teachings include those disclosed in U.S. Pat. No. 7,658,751, which issued on Feb. 9, 2010 and is assigned to Biomet Sports Medicine, LLC, Warsaw, Ind. The disclosure of U.S. Pat. No. 7,658,751 is incorporated herein by reference.

The suture construct 302 is connected to the compression member 14 such that the first loop 324 extends through the first and third suture apertures 308a and 308c, and the second loop 326 extends through the second and fourth suture apertures 308b and 308d. Attached to the sleeve portion 316 is the anchor 304. The anchor 304 generally includes an elongated anchor body 342 including a first end 344 and a second end 346 opposite to the first end 344. The anchor 304 defines an insertion tool aperture 348 at the first end and a suture aperture 350 at a position about halfway between the first end 344 and the second end 346. The sleeve portion 316 extends through the suture aperture 350 to secure the anchor 304, such as the ToggleLoc™, JuggerKnot™, or EZLoc™, to the suture construct 302.

With reference to FIGS. 25-26, a method of anchoring the compression member 14 with the suture construct 302 will now be described. After the base member 12 is impacted into the posterior wall surface 112 of the tibial tunnel 102 as described above and the bore 292 has been formed perpendicular to the tunnel longitudinal axis E, the suture construct 302 with the compression member 14 mounted thereto is inserted through the bore 292. To insert the suture construct 302 through the bore 292, an insertion rod 360 is mated with the anchor 304 and pushed through the first aperture 28 of the base member 12 and the bore 292 to the opposite side of the bone cortex 117. The anchor 304 is positioned such that it extends across the bore 292 at the cortex and the insertion rod 360 is withdrawn from the bore. To accommodate the anchor 304 and the insertion rod 360, the first aperture 28 can be enlarged and provided without threads. The graft 18 can be inserted within the tibial tunnel 102 across the base member 12 prior to or after the anchor 304 is inserted through the base member 12 and anchored to the tibia 104. Strands of the graft 18 are typically arranged on opposite sides of the suture 302, but all strands of the graft 18 may be arranged on only one side of the suture 302.

The first and the second ends 310 and 312 are arranged to extend from different ones of the suture apertures 308a-308d. When the first and second ends 310 and 312 are pulled, the first and second loops 324 and 326 become smaller, thus pulling the compression member 14 toward the base member 12 and compressing the soft tissue graft 18 therebetween. Because the suture construct 302 locks the loops 324 and 326 in the reduced size or diameter configuration, there is no need to tie knots at the first and the second ends 310 and 312.

Instead of providing the compression member 14 with the four apertures 308a-308d to receive the suture construct 302, the compression member 14 can define a first slit 370 and a second slit 372 along the second line D on opposite sides of the longitudinal axis C, as illustrated in FIG. 27. After the anchor 304 is secured against the bone cortex 117 as described above, the first and second loops 324 and 326 can be positioned within and across the first and second slits 370 and 372 to secure the suture construct 302 to the compression member 14, as illustrated in FIGS. 28 and 29. To secure the compression member 14 to the base member 12 and compress the graft 18 therebetween, the first and second ends 310 and 312 are pulled to shorten the suture loops 324 and 326, as illustrated in FIG. 30.

With additional reference to FIGS. 31 and 32, the suture construct 302 can also be secured in position with a fastener button 380. The fastener button 380 is generally disk shaped and defines a first receptacle 382a and a second receptacle 382b, which is opposite to the first receptacle 382a. After the anchor 304 is secured against the bone cortex 117 as described above and illustrated in FIG. 28, the first and second loops 324 and 326 and the first and second ends 310 and 312 can be drawn through the second aperture 68 of the compression member 14. The first and the second loops 324 and 326 can be seated within and across the first receptacle 382a and the second receptacle 382b of the fastener button 380 to secure 302 the suture to the fastener button 380. As the first and the second ends 310 and 312 of the suture construct 302 are pulled, the button 380 is pulled against the concave outer surface 62 of the compression member 14 to draw the compression member 14 against the base member 12 and compress the soft tissue graft 18 therebetween, as illustrated in FIG. 32. The button 380 can be made of any suitable material, such as a compressible material that permits the button to bend and conform to the shape of the compression member 14 when nested against the concave outer surface 62. The graft 18 can be inserted within the tibial tunnel 102 across the base member 12 prior to or after the anchor 304 is inserted through the base member 12 and anchored to the tibia 104. Strands of the graft 18 are typically arranged on opposite sides of the suture 302, but all strands of the graft 18 may be arranged on only one side of the suture 302.

With additional reference to FIGS. 33-36, the suture construct 302 can be anchored to the tibia 104 prior to the base member 12 being implanted in the tibial tunnel 102. After the anchor 304 is positioned across the bore 292 as described above and prior to the base member 12 being implanted, the first and the second suture loops 324 and 326 and the first and second suture ends 310 and 312 can be threaded through the first aperture 28 of the base member 12. The first and the second suture loops 324 and 326 can then be secured to or at the compression member 14 in any manner described above, such as within slits 370 and 372. By implanting the anchor 304 prior to implanting the base member 12, the first aperture 28 can be provided with a smaller diameter because there is no need to pass the anchor 304 through the first aperture 28. The graft 18 can be inserted within the tibial tunnel 102 across the base member 12 prior to or after the suture 302 is connected to the compression member 14. Strands of the graft 18 are typically arranged on opposite sides of the suture 302, but all strands of the graft 18 may be arranged on only one side of the suture 302.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A graft fixation system comprising:
a base member including a bone engaging surface and a first graft engaging surface opposite to the bone engaging surface;
a plurality of first fixation members extending from the bone engaging surface and configured to be impacted into bone;
a compression member including a second graft engaging surface and an outer surface opposite to the second graft engaging surface, the compression member is separate and distinct from the base member and configured to be fastened thereto; and
a fastener configured to secure the compression member relative to the base member such that a graft between the base member and the compression member is compressed therebetween and secured to the graft fixation system;
wherein the bone engaging surface is convex and the first graft engaging surface is concave to provide the base member with a curved shape in cross-section;
wherein the second graft engaging surface is convex and the outer surface is concave to provide the compression member with a curved shape in cross-section; and
wherein the first graft engaging surface is complementary to the second graft engaging surface.

2. The graft fixation system of claim 1, wherein at least one of the first graft engaging surface and the second graft engaging surface is textured.

3. The graft fixation system of claim 1, wherein the base member includes a first longitudinal axis that extends from a first end of the base member to a second end of the base member, the first end and the second end are both curved and the first longitudinal axis extends through an apex of the curve; and a first aperture defined by the base member along the first longitudinal axis at a center portion of the base member, the first aperture including threads defined therein.

4. The graft fixation system of claim 3, wherein the compression member includes a second longitudinal axis that extends from a first end of the compression member to a second end of the compression member, the first longitudinal axis is parallel to the second longitudinal axis, the first end and the second end are both curved and the second longitudinal axis extends through an apex of the curve; and a second aperture defined by the compression member along the second longitudinal axis at a center portion of the compression member;

wherein each one of the base and compression members have complementary saddle shapes.

5. The graft fixation system of claim 4, wherein the fastener is a bicortical screw configured to extend through the first aperture and the second aperture.

6. The graft fixation system of claim 1, further comprising a plurality of pointed second fixation members extending from the second graft engaging surface and configured to engage the graft.

7. The graft fixation system of claim 1, wherein the fastener includes a self-locking suture construct; and wherein the compression member defines a plurality of suture apertures configured to receive first and second loops of the self-locking suture.

8. The graft fixation system of claim 7, further comprising an anchor connected to the self-locking suture construct, the anchor configured to anchor the self-locking suture construct to bone.

9. The graft fixation system of claim 1, wherein the fastener includes a self-locking suture construct; and wherein the compression member defines a first slit opposite to a second slit, each of which are configured to receive first and second loops of the self-locking suture construct.

10. The graft fixation system of claim 1, wherein the fastener includes a self-locking suture construct; and further comprising a button defining a first slit opposite to a second slit, each of which are configured to receive first and second loops of the self-locking suture construct, the compression member is between the button and the base member.

11. The graft fixation system of claim 1, further comprising a flange extending from the base member at a position along a longitudinal axis of the base member and configured to be bent to abut an outer bone surface outside a bone hole that the base member is implanted within, the flange defining a hole configured to receive a retention member and direct the retention member into the outer bone surface.

12. The graft fixation system of claim 1, wherein the fastener includes one of a screw, a bicortical screw, or a self-locking suture construct.

13. A graft fixation system comprising:

a base member including a bone engaging surface and a first graft engaging surface opposite to the bone engaging surface, the base member includes a first longitudinal axis that extends from a first curved end of the base member to a second curved end of the base member and through a first apex of curvature of both the first curved end and the second curved end of the base member;

a compression member including a second graft engaging surface and an outer surface opposite to the second graft engaging surface, the first graft engaging surface and the second graft engaging surface are complementary to one another, the compression member includes a second longitudinal axis that extends from a first curved end of the compression member to a second curved end of the compression member and through a second apex of curvature of both the first curved end and the second curved end of the compression member, the first longitudinal axis is parallel to the second longitudinal axis;

a fastener configured to secure the compression member relative to the base member such that a graft between the base member and the compression member is compressed therebetween and secured to the graft fixation system; and a plurality of rigid first fixation members extending from the bone engaging surface and configured to be impacted into bone;

wherein the plurality of the rigid first fixation members and the base member are all one piece; and wherein the base member and the compression member are both curved in cross-section and saddle-shaped.

14. The graft fixation system of claim 13, wherein the bone engaging surface is convex and the first graft engaging surface is concave.

15. The graft fixation system of claim 14, wherein the second graft engaging surface is convex and the outer surface is concave.

16. The graft fixation system of claim 15, wherein at least one of the first graft engaging surface and the second graft engaging surface is textured.

17. The graft fixation system of claim 13, wherein a first aperture defined by the base member along the first longitudinal axis at a center portion of the base member, the first aperture including threads defined therein.

18. The graft fixation system of claim 17, wherein a second aperture defined by the compression member along the second longitudinal axis at a center portion of the compression member.

19. The graft fixation system of claim 13, further comprising a plurality of pointed second fixation members extending from the second graft engaging surface and configured to engage the graft.

20. The graft fixation system of claim 13, wherein the fastener includes a self-locking suture construct; and wherein the compression member defines a plurality of suture apertures configured to receive first and second loops of the self-locking suture.

21. The graft fixation system of claim 13, wherein the fastener includes a self-locking suture construct; and wherein the compression member defines a first slit opposite to a second slit, each of which are configured to receive first and second loops of the self-locking suture construct.

22. The graft fixation assembly of claim 13, wherein the compression member is separate and distinct from the base member and configured to be fastened thereto; and further comprising a flange extending from the base member at a position along the first longitudinal axis of the base member and configured to be bent to abut an outer bone surface outside a bone hole that the base member is implanted within, the flange defining a hole configured to receive a retention member and direct the retention member into the outer bone surface.

23. A graft fixation system comprising:

a base member including a convex bone engaging surface and a concave first graft engaging surface opposite to the convex bone engaging surface, the concave first graft engaging surface is generally saddle-shaped to receive a graft thereon, the base member includes a first longitudinal axis that extends from a first end of the base member to a second end of the base member, the first and the second ends of the base member are rounded;

a first aperture defined by the base member along the first longitudinal axis at a center portion of the base member, the first aperture including threads defined therein;

a plurality of first fixation members extending from the convex bone engaging surface and configured to be impacted into bone;

a compression member including a convex second graft engaging surface and a concave outer surface opposite to the convex second graft engaging surface, the convex second graft engaging surface is curved to generally compress any graft between the base member and the compression member against the concave first graft engaging surface when the compression member and the base member are drawn together, the compression member is separate and distinct from the base member and configured to be coupled thereto, the compression member includes a second longitudinal axis that extends from a first end of the compression member to a second end of the compression member when the compression and base members are coupled together, the first longitudinal axis is parallel to the second longitudinal axis, the first and the second ends are curved, the first longitudinal axis extends through a first apex of curvature of the first end and the second longitudinal axis extends through a second apex of curvature of the second end;

a second aperture defined by the compression member along the second longitudinal axis at a center portion of the compression member; and a flange extending from the first end of the base member and defining a third aperture, the third aperture configured to receive and direct a bone engaging member into an external bone surface.

24. The graft fixation system of claim 23, further comprising a fastener configured to secure the compression member relative to the base member to compress any graft therebetween and secure the graft to the graft fixation system.

25. The graft fixation system of claim 23, wherein each of the base member and the compression member have a curved shape in cross-section.

26. The graft fixation system of claim 23, wherein the concave first graft engaging surface is complementary to the convex second graft engaging surface.

27. The graft fixation system of claim 23, wherein the fastener is a bicortical screw configured to extend through the first aperture and the second aperture.

28. The graft fixation system of claim 23, wherein the plurality of first fixation members and the base member are all one piece.

29. The graft fixation system of claim 23, wherein the plurality of first fixation members and the base member are monolithic.

30. The graft fixation system of claim 23, further comprising a plurality of second fixation members extending from the convex second graft engaging surface.

31. The graft fixation system of claim 23, further comprising a flange extending from the base member at a position along the first longitudinal axis of the base member and configured to be bent to abut an outer bone surface outside a bone hole that the base member is implanted within, the flange defining a hole configured to receive a retention member and direct the retention member into the outer bone surface.

* * * * *